(12) United States Patent
Abercrombie et al.

(10) Patent No.: US 10,494,590 B2
(45) Date of Patent: Dec. 3, 2019

(54) CLEANING MATERIAL

(71) Applicant: Xeros Limited, Rotherham (GB)

(72) Inventors: Elizabeth Jean Abercrombie, Glasgow (GB); Ana America Tellechea Lopez, Sheffield (GB); John Edward Steele, Leeds (GB); Stephen Derek Jenkins, Middlesbrough (GB)

(73) Assignee: Xeros Limited, Rotherham, South Yorkshire (GB)

( * ) Notice: Subject to any disclaimer, the term of this patent is extended or adjusted under 35 U.S.C. 154(b) by 668 days.

(21) Appl. No.: 14/412,298

(22) PCT Filed: Jul. 8, 2013

(86) PCT No.: PCT/GB2013/051795
§ 371 (c)(1),
(2) Date: Dec. 31, 2014

(87) PCT Pub. No.: WO2014/006424
PCT Pub. Date: Jan. 9, 2014

(65) Prior Publication Data
US 2015/0152357 A1 Jun. 4, 2015

(30) Foreign Application Priority Data

Jul. 6, 2016 (GB) .................................. 1212098.6

(51) Int. Cl.
| | | |
|---|---|---|
| C11D 3/37 | (2006.01) | |
| C11D 3/386 | (2006.01) | |
| C11D 3/39 | (2006.01) | |
| C11D 3/395 | (2006.01) | |
| C11D 7/06 | (2006.01) | |
| C11D 7/10 | (2006.01) | |
| C11D 7/32 | (2006.01) | |
| C11D 17/00 | (2006.01) | |
| D06L 1/00 | (2017.01) | |

(52) U.S. Cl.
CPC ........ *C11D 3/3719* (2013.01); *C11D 3/38681* (2013.01); *C11D 3/3902* (2013.01); *C11D 3/3951* (2013.01); *C11D 7/06* (2013.01); *C11D 7/10* (2013.01); *C11D 7/3263* (2013.01); *C11D 17/0039* (2013.01); *D06L 1/00* (2013.01)

(58) Field of Classification Search
CPC ....... C11D 3/3719; C11D 3/37; C11D 3/3715; C11D 3/3726; C11D 3/3749; C11D 17/0034; C12N 11/08; C12N 11/14
See application file for complete search history.

(56) References Cited

U.S. PATENT DOCUMENTS

| | | |
|---|---|---|
| 2,970,464 A | 2/1961 | Toma |
| 3,321,843 A | 5/1967 | Taran et al. |
| 3,333,344 A | 8/1967 | Loewen |
| 3,647,354 A | 3/1972 | Loeb |
| 3,650,673 A | 3/1972 | Ehner |
| 3,805,406 A | 4/1974 | Castonoli |
| 4,055,248 A | 10/1977 | Marsan |
| 4,130,392 A | 12/1978 | Diehl et al. |
| 4,188,807 A | 2/1980 | Graf et al. |
| 4,326,971 A | 4/1982 | Wixon |
| 4,374,443 A | 2/1983 | Mosell |
| 4,434,067 A | 2/1984 | Malone et al. |
| 4,493,783 A | 1/1985 | Su et al. |
| 4,575,887 A | 3/1986 | Viramontes |
| 4,637,890 A | 1/1987 | Crabtree et al. |
| 4,655,952 A | 4/1987 | Mesmer et al. |
| 4,750,227 A | 6/1988 | Hopkins et al. |
| 4,761,249 A * | 8/1988 | Giede .................. C11D 3/0036 252/179 |
| 4,801,333 A | 1/1989 | Mosell |

(Continued)

FOREIGN PATENT DOCUMENTS

| | | |
|---|---|---|
| CA | 1284407 C | 5/1991 |
| CA | 2147207 A1 | 5/1994 |

(Continued)

OTHER PUBLICATIONS

Shukla et al, Imobilisation of amylase by various techniques, Mar. 2005, Indian Journal of Fibre & Textile Research, vol. 29 pp. 75-81.*
bc.edu, Experiment 16: Polymers, Feb. 1, 2002, bc.edu, date stampe and 4 passages of text.*
Sharan, Garment Washing, Oct. 23, 2011, Rajeev Sharan, date stamp, and 7 paages.*
Brena et al, Immobilization of Enzymes, 2006, Humana Press, Fig2, 1 passage of text from 5.1 Adsorption(Noncovalent Interactions).*
U.S. Appl. No. 15/344,120, He et al.
U.S. Appl. No. 15/510,569, Xeros Ltd.
U.S. Appl. No. 15/510,576, Xeros Ltd.
U.S. Appl. No. 15/513,014, Xeros Ltd.

(Continued)

*Primary Examiner* — Mikhail Kornakov
*Assistant Examiner* — Natasha N Campbell
(74) *Attorney, Agent, or Firm* — Clark & Elbing LLP

(57) ABSTRACT

The invention provides a cleaning formulation comprising a multiplicity of solid cleaning particles, wherein the solid cleaning particles comprise polymeric particles and at least one cleaning agent, wherein the at least one cleaning agent is immobilised on the surface of the polymeric particles. Typically the at least one cleaning agent is immobilised on the surface of the polymeric particles by means of chemical bonds, typically ionic bonds, hydrogen bonds, covalent bonds, polar bonds, or bonds formed by virtue of unequal charge distributions between polymeric particles and immobilised materials. The invention also provides a method for the cleaning of a substrate, the method comprising the treatment of the substrate with a formulation according to the invention, and a method for the preparation of the cleaning formulation of the invention which comprises treating a multiplicity of polymeric particles with at least one cleaning agent.

14 Claims, 6 Drawing Sheets

(56) References Cited

U.S. PATENT DOCUMENTS

| | | |
|---|---|---|
| 4,809,854 A | 3/1989 | Tomaszek |
| 4,839,969 A | 6/1989 | Hahn |
| 4,951,366 A | 8/1990 | Geller |
| 4,978,619 A | 12/1990 | Kajiwara et al. |
| 5,245,722 A | 9/1993 | Dameron |
| 5,305,533 A | 4/1994 | Alexander et al. |
| 5,324,649 A | 6/1994 | Arnold et al. |
| 5,367,734 A | 11/1994 | Terry |
| 5,468,175 A | 11/1995 | Nilen |
| 5,475,992 A | 12/1995 | Wiegert |
| 5,503,840 A | 4/1996 | Jacobson et al. |
| 5,547,476 A | 8/1996 | Siklosi et al. |
| 5,601,480 A | 2/1997 | Nilen |
| 5,605,491 A | 2/1997 | Yam et al. |
| 5,667,431 A | 9/1997 | Mortin |
| 5,804,548 A | 9/1998 | Davis |
| 5,849,684 A | 12/1998 | Donoghue et al. |
| 5,925,195 A | 7/1999 | King et al. |
| 5,978,994 A | 11/1999 | Anderson |
| 5,980,620 A | 11/1999 | Brodie et al. |
| 5,993,839 A | 11/1999 | Mixon |
| 6,235,705 B1 | 5/2001 | Zembrodt et al. |
| 6,348,441 B1 | 2/2002 | Aiken, III et al. |
| 6,376,046 B1 | 4/2002 | Hoshino et al. |
| 6,448,212 B1 | 9/2002 | Holderbaum et al. |
| 7,070,489 B2 | 7/2006 | Rogmark |
| 7,097,715 B1 | 8/2006 | Racette et al. |
| 7,481,893 B2 | 1/2009 | Motson et al. |
| 7,498,294 B2 | 3/2009 | Konno et al. |
| 8,959,961 B2 | 2/2015 | Jenkins et al. |
| 8,974,545 B2 | 3/2015 | Burkinshaw et al. |
| 9,017,423 B2 | 4/2015 | Burkinshaw et al. |
| 9,121,000 B2 | 9/2015 | Burkinshaw et al. |
| 9,127,882 B2 | 9/2015 | Jenkins et al. |
| 9,297,107 B2 | 3/2016 | Jenkins |
| 9,315,766 B2 | 4/2016 | He et al. |
| 9,404,210 B2 | 8/2016 | He et al. |
| 9,410,278 B2 | 8/2016 | He et al. |
| 9,476,155 B2 | 10/2016 | He et al. |
| 9,487,898 B2 | 11/2016 | He et al. |
| 9,523,169 B2 | 12/2016 | Sawford et al. |
| 9,550,966 B2 | 1/2017 | Burkinshaw et al. |
| 9,587,337 B2 | 3/2017 | He et al. |
| 9,587,340 B2 | 3/2017 | Jenkins et al. |
| 9,631,314 B2 | 4/2017 | Yin et al. |
| 9,803,307 B2 | 10/2017 | Jenkins et al. |
| 9,834,881 B2 | 12/2017 | Sawford et al. |
| 9,845,516 B2 | 12/2017 | Steele |
| 9,850,455 B2 | 12/2017 | Jenkins et al. |
| 9,850,619 B2 | 12/2017 | Wells et al. |
| 9,914,901 B2 | 3/2018 | Burkinshaw et al. |
| 9,932,700 B2 | 4/2018 | Wells et al. |
| 10,017,895 B2 | 7/2018 | Wells et al. |
| 10,081,900 B2 | 9/2018 | Wells et al. |
| 10,287,642 B2 | 5/2019 | Scott |
| 2001/0031714 A1 | 10/2001 | Gassenmeier et al. |
| 2002/0010300 A1 | 1/2002 | Mimoun |
| 2002/0016282 A1 | 2/2002 | Kumar et al. |
| 2002/0022050 A1 | 2/2002 | Anderson et al. |
| 2002/0039976 A1 | 4/2002 | Sebillotte-Arnaud et al. |
| 2002/0058595 A1 | 5/2002 | Kaiser |
| 2002/0133886 A1 | 9/2002 | Severns et al. |
| 2003/0110580 A1 | 6/2003 | Burkinshaw et al. |
| 2003/0134759 A1 | 7/2003 | Geary et al. |
| 2004/0025262 A1 | 2/2004 | Hamers et al. |
| 2004/0171515 A1 | 9/2004 | Hamers et al. |
| 2004/0242133 A1 | 12/2004 | Arellano et al. |
| 2004/0266641 A1 | 12/2004 | Gentschev et al. |
| 2005/0028564 A1 | 2/2005 | Lee et al. |
| 2005/0148479 A1 | 7/2005 | Barthel et al. |
| 2005/0153865 A1 | 7/2005 | Detering et al. |
| 2005/0183206 A1 | 8/2005 | Brown et al. |
| 2005/0183208 A1 | 8/2005 | Scheper et al. |
| 2005/0204477 A1 | 9/2005 | Casella et al. |
| 2006/0189506 A1 | 8/2006 | Muller et al. |
| 2006/0287212 A1 | 12/2006 | Sommer et al. |
| 2007/0151312 A1 | 7/2007 | Bruce et al. |
| 2007/0256251 A1* | 11/2007 | Orlich ............ C11D 3/38618 8/137 |
| 2007/0270327 A1 | 11/2007 | Beck et al. |
| 2008/0090746 A1 | 4/2008 | Penninger |
| 2008/0223406 A1 | 9/2008 | Lindqvist et al. |
| 2008/0276965 A1 | 11/2008 | Aykroyd et al. |
| 2008/0306183 A1 | 12/2008 | Leukel et al. |
| 2009/0090138 A1 | 4/2009 | Wang |
| 2009/0186795 A1 | 7/2009 | Feenstra et al. |
| 2009/0217461 A1 | 9/2009 | Burkinshaw et al. |
| 2009/0276966 A1 | 11/2009 | Mette et al. |
| 2010/0281928 A1 | 11/2010 | Martin |
| 2011/0296628 A1 | 12/2011 | Jenkins et al. |
| 2012/0048299 A1 | 3/2012 | Jenkins et al. |
| 2012/0060350 A1 | 3/2012 | Kwon et al. |
| 2012/0111359 A1 | 5/2012 | Mueller et al. |
| 2012/0225025 A1 | 9/2012 | Lang |
| 2012/0284931 A1 | 11/2012 | Jenkins et al. |
| 2012/0304400 A1 | 12/2012 | Jenkins et al. |
| 2013/0061404 A1 | 3/2013 | Jenkins |
| 2013/0167882 A1 | 7/2013 | Burkinshaw et al. |
| 2013/0276242 A1 | 10/2013 | Jenkins et al. |
| 2013/0281345 A1 | 10/2013 | Burkinshaw et al. |
| 2013/0283542 A1 | 10/2013 | Jenkins et al. |
| 2013/0305560 A1 | 11/2013 | Jenkins et al. |
| 2013/0340487 A1 | 12/2013 | Yin et al. |
| 2014/0123402 A1 | 5/2014 | He et al. |
| 2014/0137340 A1 | 5/2014 | Burkinshaw et al. |
| 2014/0201929 A1 | 7/2014 | He et al. |
| 2014/0317860 A1 | 10/2014 | He et al. |
| 2015/0027173 A1 | 1/2015 | Wu et al. |
| 2015/0096128 A1 | 4/2015 | Sawford et al. |
| 2015/0096129 A1 | 4/2015 | Sawford et al. |
| 2015/0128358 A1 | 5/2015 | Wells et al. |
| 2015/0148278 A1 | 5/2015 | Burkinshaw et al. |
| 2015/0152357 A1 | 6/2015 | Abercrombie et al. |
| 2015/0152585 A1 | 6/2015 | Sawford et al. |
| 2015/0175945 A1 | 6/2015 | Waddon et al. |
| 2015/0252511 A1 | 9/2015 | Roberts et al. |
| 2016/0032522 A1 | 2/2016 | Steele |
| 2016/0040260 A1 | 2/2016 | Steele |
| 2016/0122932 A1 | 5/2016 | Wells et al. |
| 2016/0122936 A1 | 5/2016 | Wells et al. |
| 2016/0195409 A1 | 7/2016 | Goldberg et al. |
| 2016/0197998 A1 | 7/2016 | Carleo |
| 2016/0251602 A1 | 9/2016 | Steele et al. |
| 2016/0251603 A1 | 9/2016 | Steele et al. |
| 2016/0251795 A1 | 9/2016 | Wells et al. |
| 2017/0051447 A1 | 2/2017 | He et al. |
| 2017/0137983 A1 | 5/2017 | He et al. |
| 2017/0159222 A1 | 6/2017 | Jenkins et al. |
| 2017/0240980 A1 | 8/2017 | Feyisa et al. |
| 2017/0240981 A1 | 8/2017 | Scott |
| 2017/0240982 A1 | 8/2017 | Sadeghi |
| 2017/0241061 A1 | 8/2017 | Wells et al. |
| 2017/0247771 A1 | 8/2017 | Scott |
| 2017/0267949 A1 | 9/2017 | Bird et al. |
| 2018/0057777 A1 | 3/2018 | Waddon et al. |
| 2018/0127914 A1 | 5/2018 | Wells et al. |
| 2018/0134994 A1 | 5/2018 | Steele et al. |
| 2018/0141089 A1 | 5/2018 | Sawford et al. |
| 2018/0216049 A1 | 8/2018 | Bird et al. |

FOREIGN PATENT DOCUMENTS

| | | |
|---|---|---|
| CN | 1256710 A | 6/2000 |
| CN | 2789299 Y | 6/2006 |
| CN | 101006108 A | 7/2007 |
| CN | 101784652 A | 7/2010 |
| CN | 101885605 A | 11/2010 |
| CN | 101886321 A | 11/2010 |
| CN | 102061589 A | 5/2011 |
| CN | 202175862 U | 3/2012 |
| CN | 102425053 A | 4/2012 |
| CN | 102425055 A | 4/2012 |
| CN | 202214631 U | 5/2012 |
| CN | 202214633 U | 5/2012 |

(56) References Cited

FOREIGN PATENT DOCUMENTS

| | | |
|---|---|---|
| CN | 202298219 U | 7/2012 |
| CN | 202298220 U | 7/2012 |
| CN | 202298222 U | 7/2012 |
| CN | 202323458 U | 7/2012 |
| CN | 202359387 U | 8/2012 |
| CN | 202359388 U | 8/2012 |
| CN | 202359389 U | 8/2012 |
| CN | 202359390 U | 8/2012 |
| CN | 202359396 U | 8/2012 |
| CN | 202401272 U | 8/2012 |
| CN | 202492706 U | 10/2012 |
| CN | 202500017 U | 10/2012 |
| CN | 202543634 U | 11/2012 |
| CN | 202543635 U | 11/2012 |
| CN | 202543646 U | 11/2012 |
| CN | 202543652 U | 11/2012 |
| CN | 102899848 A | 1/2013 |
| CN | 202688698 U | 1/2013 |
| CN | 202755220 U | 2/2013 |
| CN | 202755221 U | 2/2013 |
| CN | 102953249 A | 3/2013 |
| CN | 102953250 A | 3/2013 |
| CN | 102953262 A | 3/2013 |
| CN | 102978870 A | 3/2013 |
| CN | 103061084 A | 4/2013 |
| CN | 103061085 A | 4/2013 |
| CN | 103061086 A | 4/2013 |
| CN | 103061087 A | 4/2013 |
| CN | 103087839 A | 5/2013 |
| CN | 103103720 A | 5/2013 |
| CN | 103103721 A | 5/2013 |
| CN | 103122566 A | 5/2013 |
| CN | 103122567 A | 5/2013 |
| CN | 202913242 U | 5/2013 |
| CN | 103225192 A | 7/2013 |
| CN | 203049283 U | 7/2013 |
| CN | 103361934 A | 10/2013 |
| CN | 103361938 A | 10/2013 |
| CN | 203370359 U | 1/2014 |
| CN | 102061588 B | 2/2014 |
| CN | 103556439 A | 2/2014 |
| CN | 203530695 U | 4/2014 |
| CN | 203530700 U | 4/2014 |
| CN | 203530714 U | 4/2014 |
| CN | 203530718 U | 4/2014 |
| CN | 203530723 U | 4/2014 |
| CN | 203530725 U | 4/2014 |
| CN | 103285643 A | 4/2015 |
| CN | 103451894 A | 11/2015 |
| CN | 103556434 B | 11/2015 |
| CN | 103556436 B | 11/2015 |
| CN | 103556431 A | 1/2016 |
| CN | 103556432 B | 3/2016 |
| CN | 105420992 A | 3/2016 |
| CN | 105420993 A | 3/2016 |
| CN | 105421000 A | 3/2016 |
| CN | 105442267 A | 3/2016 |
| CN | 205329373 U | 6/2016 |
| CN | 205329374 U | 6/2016 |
| CN | 205329380 U | 6/2016 |
| CN | 205329384 U | 6/2016 |
| DE | 1900002 A1 | 7/1970 |
| DE | 2819233 A1 | 11/1979 |
| DE | 3803195 A1 | 8/1989 |
| DE | 19505921 A1 | 8/1996 |
| DE | 10247289 A1 | 4/2004 |
| DE | 102007029485 A1 | 1/2009 |
| DE | 102008009462 A1 | 8/2009 |
| DE | 102009046170 A1 | 5/2011 |
| EP | 0090372 A1 | 10/1983 |
| EP | 0171215 A1 | 2/1986 |
| EP | 0312278 A2 | 4/1989 |
| EP | 0807463 A2 | 11/1997 |
| EP | 1371718 A1 | 12/2003 |
| EP | 2103677 A1 | 9/2009 |
| FR | 2525645 A1 | 10/1983 |
| FR | 2826548 A1 | 1/2003 |
| GB | 1018318.4 | 1/1966 |
| GB | 920791 A | 3/1968 |
| GB | 1256064 A | 12/1971 |
| GB | 1297316 A | 11/1972 |
| GB | 1379742 A | 1/1975 |
| GB | 2249104 A | 4/1992 |
| GB | 2302553 A | 1/1997 |
| GB | 2365648 A | 2/2002 |
| GB | 2456407 A | 7/2009 |
| GB | 2473224 A | 3/2011 |
| JP | S59-48078 A | 3/1984 |
| JP | S59-196758 A | 11/1984 |
| JP | H01285188 A | 11/1989 |
| JP | H0257295 A | 2/1990 |
| JP | H03-146094 B2 | 6/1991 |
| JP | H04105633 A | 7/1992 |
| JP | H04241165 A | 8/1992 |
| JP | H06240297 A | 8/1994 |
| JP | 2004-167345 A | 6/2004 |
| JP | 2004238602 A | 8/2004 |
| JP | 2006-326434 A | 12/2006 |
| WO | WO-98/37270 A1 | 8/1998 |
| WO | WO-98/42818 A1 | 10/1998 |
| WO | WO-99/40251 A1 | 8/1999 |
| WO | WO-00/37540 A1 | 6/2000 |
| WO | WO-00/77153 A1 | 12/2000 |
| WO | WO-02/42403 A1 | 5/2002 |
| WO | WO-03/054128 A1 | 7/2003 |
| WO | WO-2004/066970 A1 | 8/2004 |
| WO | WO-2006/020789 A1 | 2/2006 |
| WO | WO-2006/040539 A1 | 4/2006 |
| WO | WO-2007/070520 A1 | 6/2007 |
| WO | WO-2007/128962 A1 | 11/2007 |
| WO | WO-2008/132456 A1 | 11/2008 |
| WO | WO-2009/021919 A2 | 2/2009 |
| WO | WO-2009/032615 A1 | 3/2009 |
| WO | WO-2009/112296 A1 | 9/2009 |
| WO | WO-2009/134018 A2 | 11/2009 |
| WO | WO-2010/046473 A1 | 4/2010 |
| WO | WO-2010/094959 A1 | 8/2010 |
| WO | WO-2010/128337 A2 | 11/2010 |
| WO | WO-2010/133837 A1 | 11/2010 |
| WO | WO-2010139689 A1 | 12/2010 |
| WO | WO-2011/015429 A2 | 2/2011 |
| WO | WO-2011/051140 A1 | 5/2011 |
| WO | WO-2011/064581 A1 | 6/2011 |
| WO | WO-2011/098815 A1 | 8/2011 |
| WO | WO-2011/128676 A1 | 10/2011 |
| WO | WO-2011/128680 A2 | 10/2011 |
| WO | WO-2012/035342 A1 | 3/2012 |
| WO | WO-2012/035343 A1 | 3/2012 |
| WO | WO-2012/056252 A2 | 5/2012 |
| WO | WO-2012/084619 A1 | 6/2012 |
| WO | WO-2012/095677 A2 | 7/2012 |
| WO | WO-2012/098408 A2 | 7/2012 |
| WO | WO-2012/104861 A1 | 8/2012 |
| WO | WO-2012/140442 A1 | 10/2012 |
| WO | WO-2014/006425 A1 | 1/2014 |
| WO | WO-2014/037729 A1 | 3/2014 |
| WO | WO-2015/004444 A1 | 1/2015 |

OTHER PUBLICATIONS

U.S. Appl. No. 15/513,309, Xeros Ltd.
U.S. Appl. No. 15/518,047, Xeros Ltd.
U.S. Appl. No. 15/532,137, Xeros Ltd.
U.S. Appl. No. 16/093,398, Xeros Ltd.
U.S. Appl. No. 16/093,433, Xeros Ltd.
U.S. Appl. No. 16/093,449, Xeros Ltd.
U.S. Appl. No. 16/318,192, Xeros Ltd.
U.S. Appl. No. 14/412,109, Xeros Ltd.
U.S. Appl. No. 14/427,046, Xeros Ltd.
U.S. Appl. No. 14/505,978, Xeros Ltd.
U.S. Appl. No. 14/505,964, Xeros Ltd.
U.S. Appl. No. 14/537,314, Xeros Ltd.
U.S. Appl. No. 14/550,359, Xeros Ltd.

(56) References Cited

OTHER PUBLICATIONS

U.S. Appl. No. 14/577,285, Xeros Ltd.
U.S. Appl. No. 14/588,500, Xeros Ltd.
U.S. Appl. No. 14/588,510, Xeros Ltd.
"Aqua Ball Set", <http://www.auravita.com/products/AURA/TAPR10610.asp>, retrieved on Aug. 14, 2006 (3 pages).
"Capture Carpet Cleaning Kit", <http://www.basichomeshopping.com/CaptureCarpetCleanerKit.html>, retrieved on Aug. 11, 2005 (4 pages).
"Capture Carpet Cleaning Kit", <http://www.domesticsale.com/Classifieds/15175.html>, retrieved on Aug. 11, 2005 (1 page).
Michalon et al., "Enzyme coupling method on calibrated nylon spheres: application to the selective trypsinization of histones in chromatin," Biochem Biophys Res Commun. 167(1):9-15 (1990).
International Search Report for PCT/GB2013/051795, dated Nov. 12, 2013 (6 pages).
Migneault et al., "Glutaraldehyde: behavior in aqueous solution, reaction with proteins, and application to enzyme crosslinking," Biotechniques. 37(5):790-802 (2004).
Silva et al., "Laccase immobilization on enzymatically functionalized polyamide 6,6 fibres," Enzyme Microb Technol. 41:867-75 (2007).
Talbert et al., "Chitosan-tethered microspheres for lactase immobilization," J Mol Catal B Enzym. 78:78-84 (2012).

\* cited by examiner

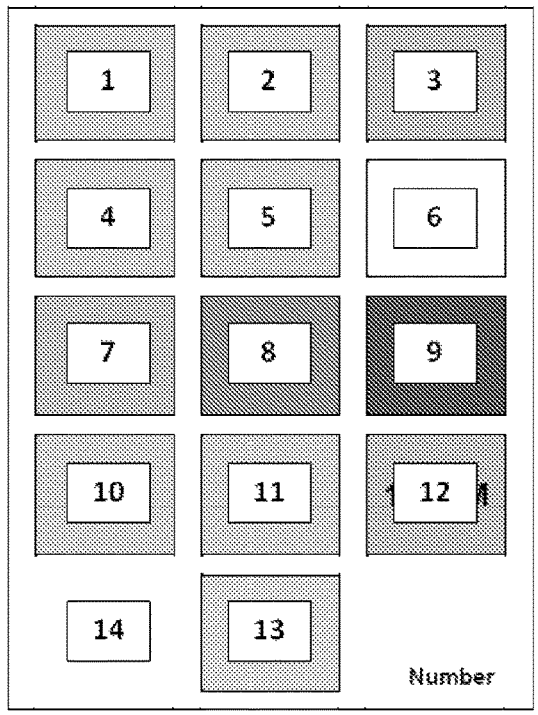
FIGURE 1    WKF STAIN SHEET TEMPLATE
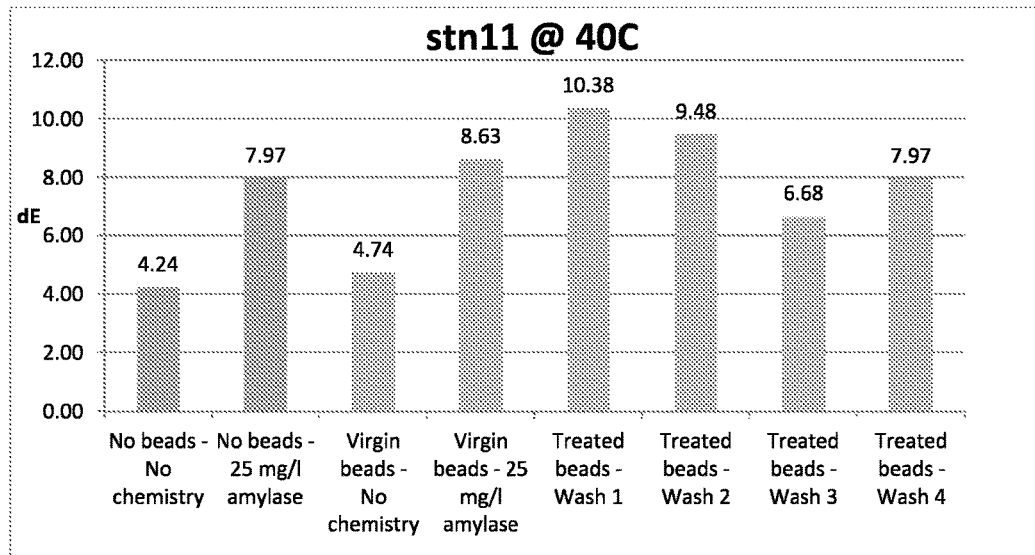
FIGURE 2    STAIN 11 AFTER WASHING AT 40°C WITH AMYLASE TREATED BEADS

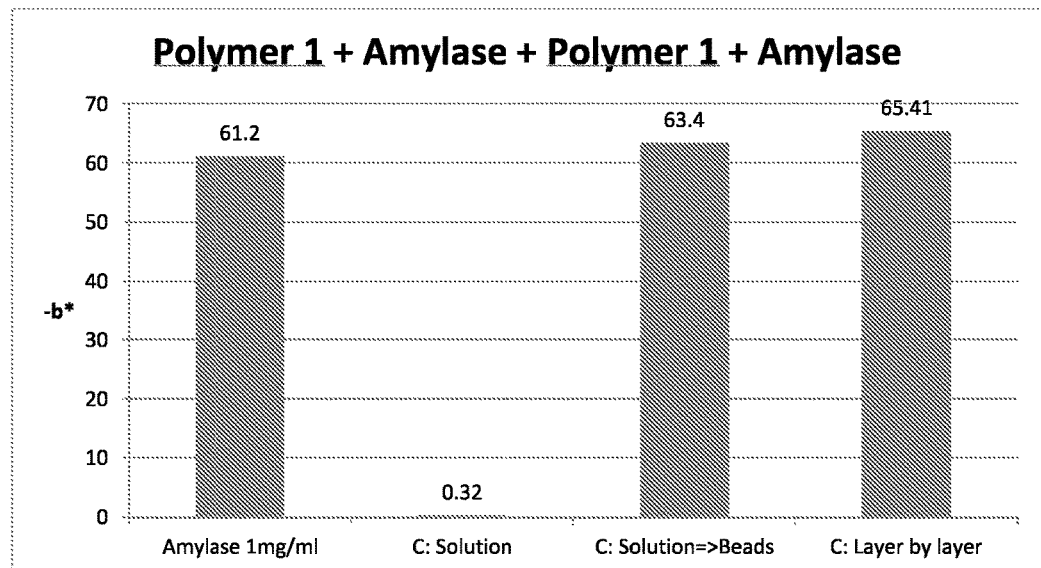
FIGURE 3    AMYLASE ACTIVITY OF POLYMER 1/AMYLASE IN SOLUTION AND AFTER TREATMENT OF BEADS
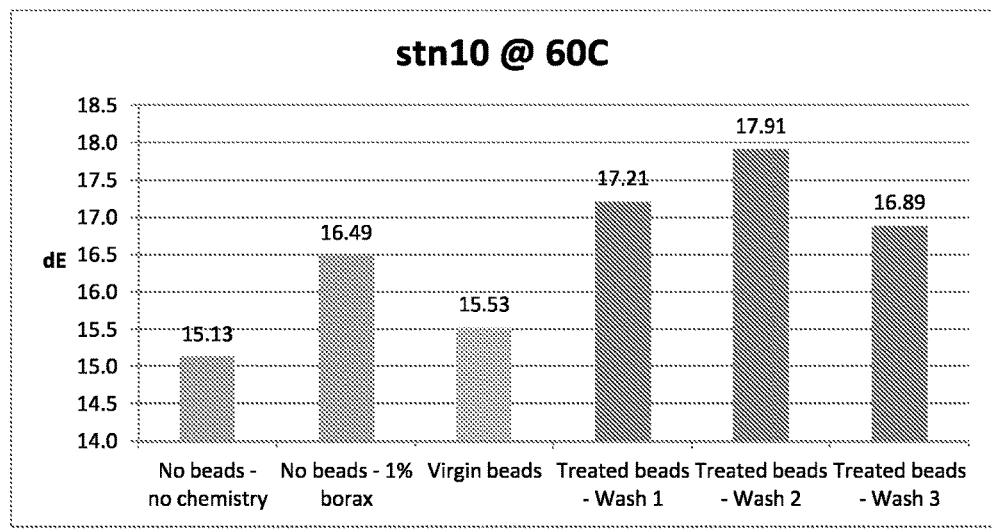
FIGURE 4    STAIN 10 AFTER WASHING WITH BORAX AT 60°C

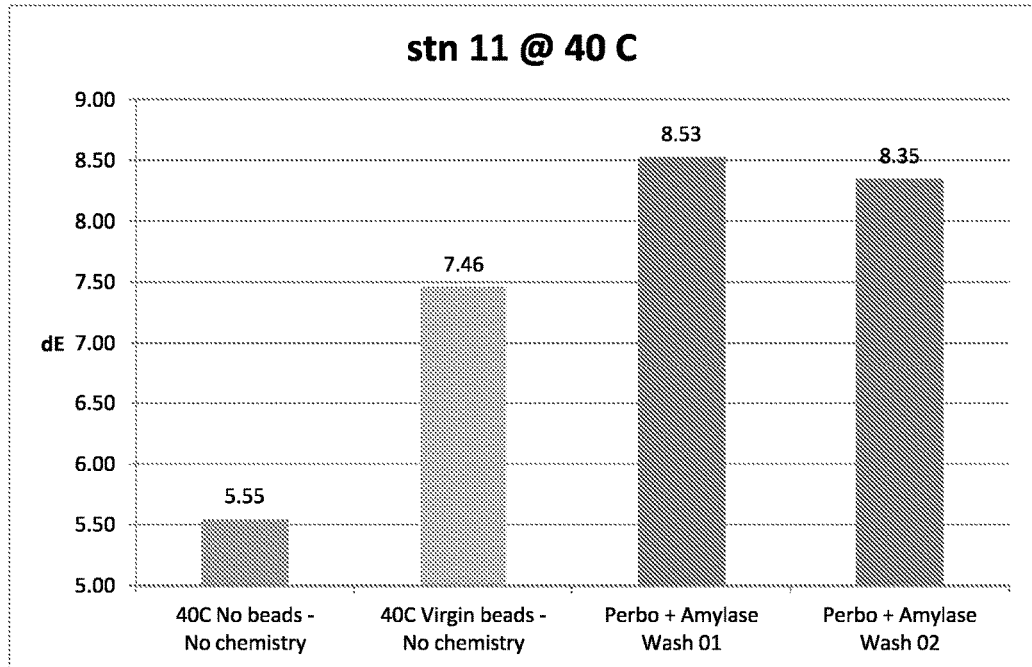
FIGURE 5  STAIN 11 (STARCH) WASHED WITH BEADS TREATED WITH AMYLASE AND PERBORATE
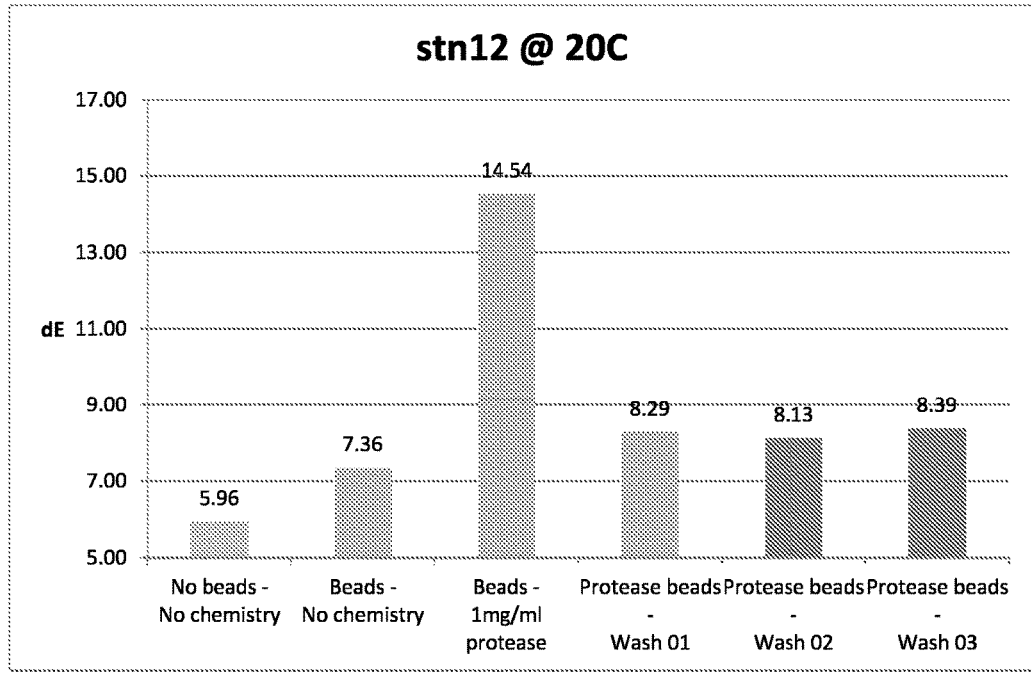
FIGURE 6  STAIN 12 WASHED WITH BEADS TREATED WITH PROTEASE

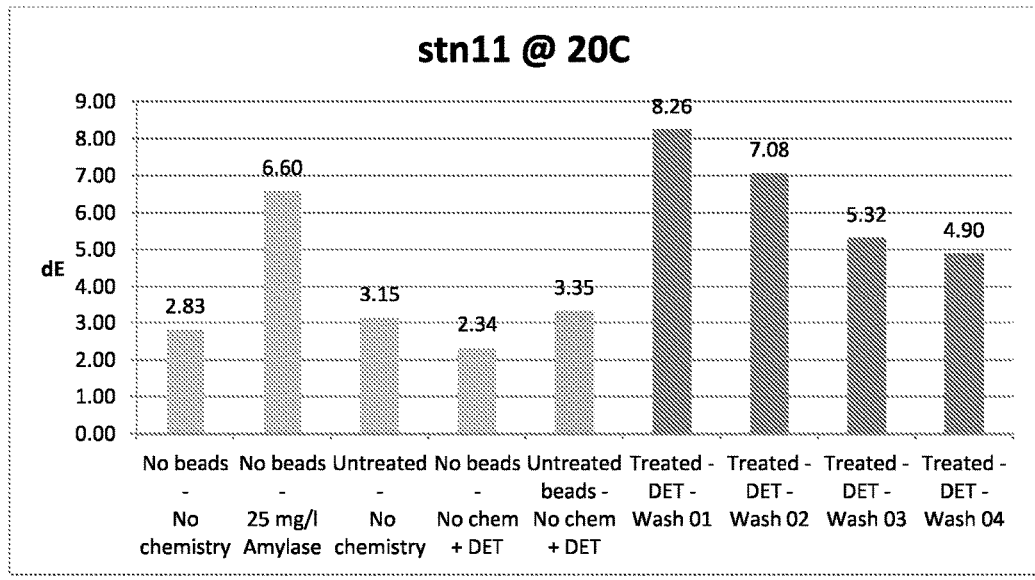
FIGURE 7 STAIN 11 (STARCH) WASHED WITH FORMULATION COMPRISING DETERGENT AND BEADS TREATED WITH AMYLASE
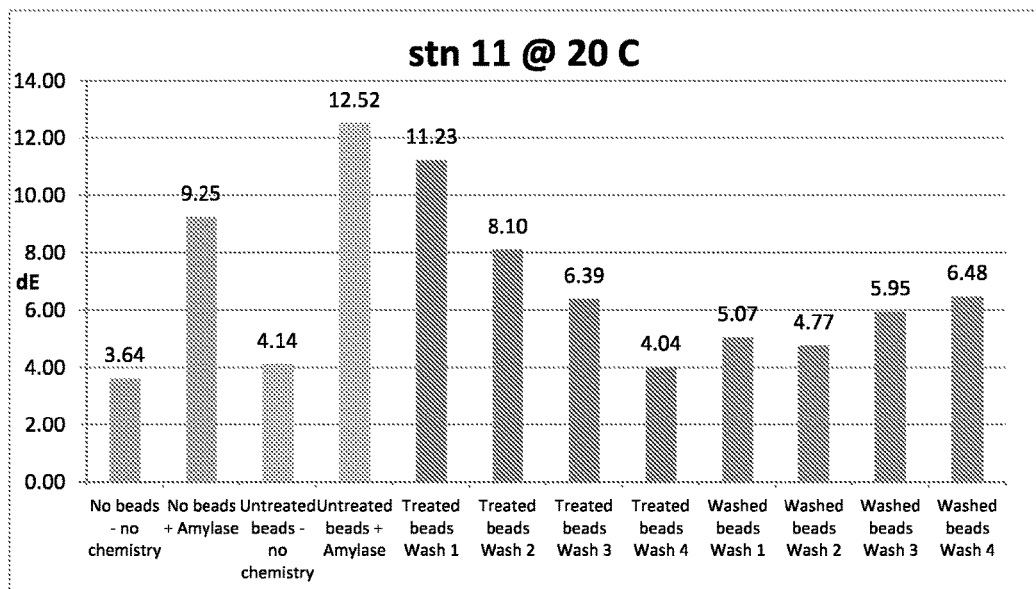
FIGURE 8 STAIN 11 (STARCH) WASHED WITH BEADS TREATED WITH AMYLASE BEFORE AND AFTER WASHING WITH SURFACTANT

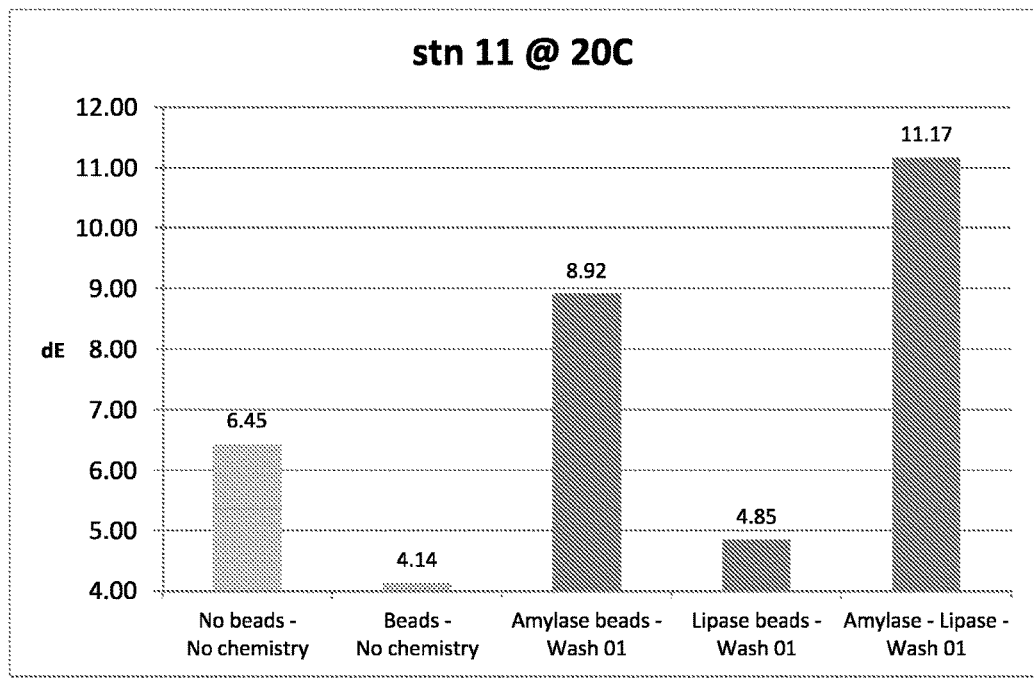
FIGURE 9    STAIN 11 WASHED WITH BEADS TREATED WITH AMYLASE AND LIPASE
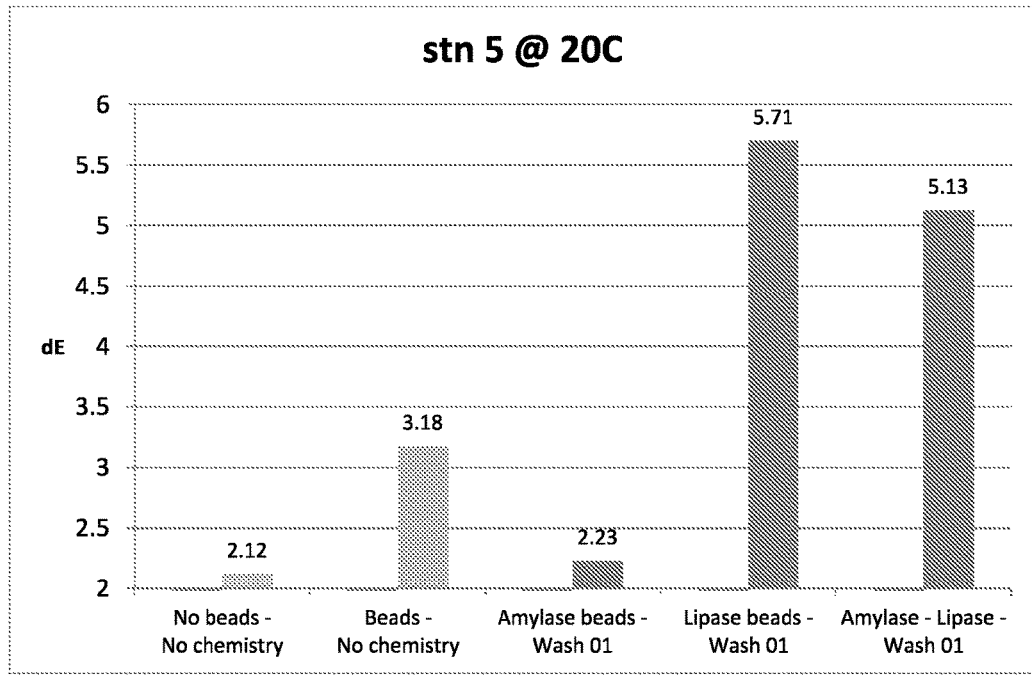
FIGURE 10   STAIN 5 WASHED WITH BEADS TREATED WITH AMYLASE AND LIPASE

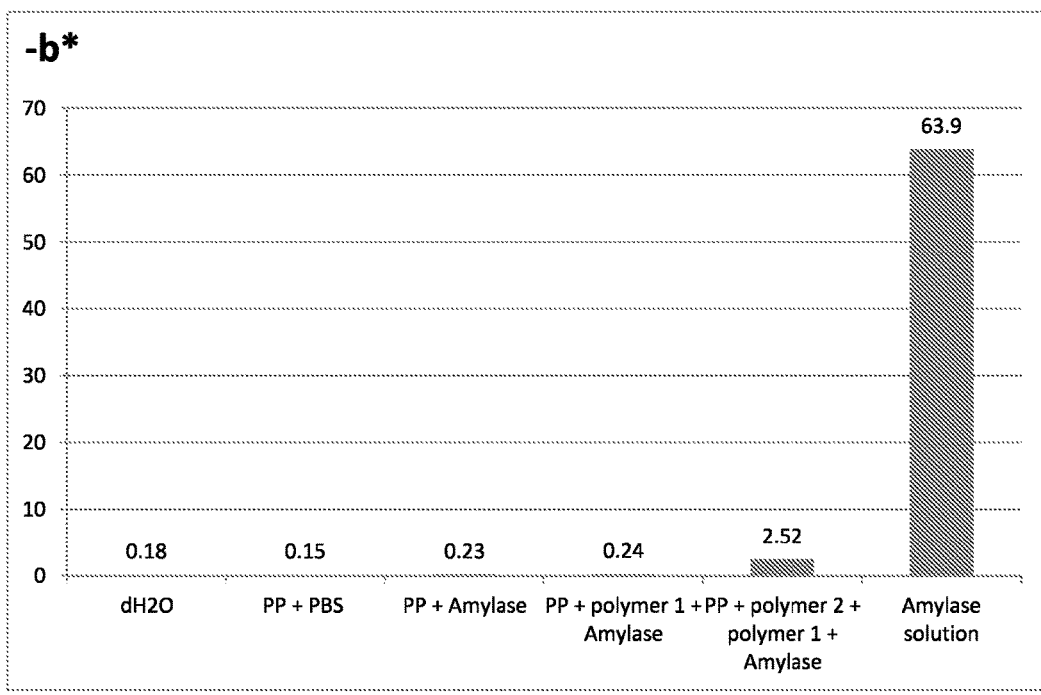
FIGURE 11  MODIFIED PHADEBAS® TEST ON POLYPROPYLENE BEADS (PP) TREATED WITH AMYLASE
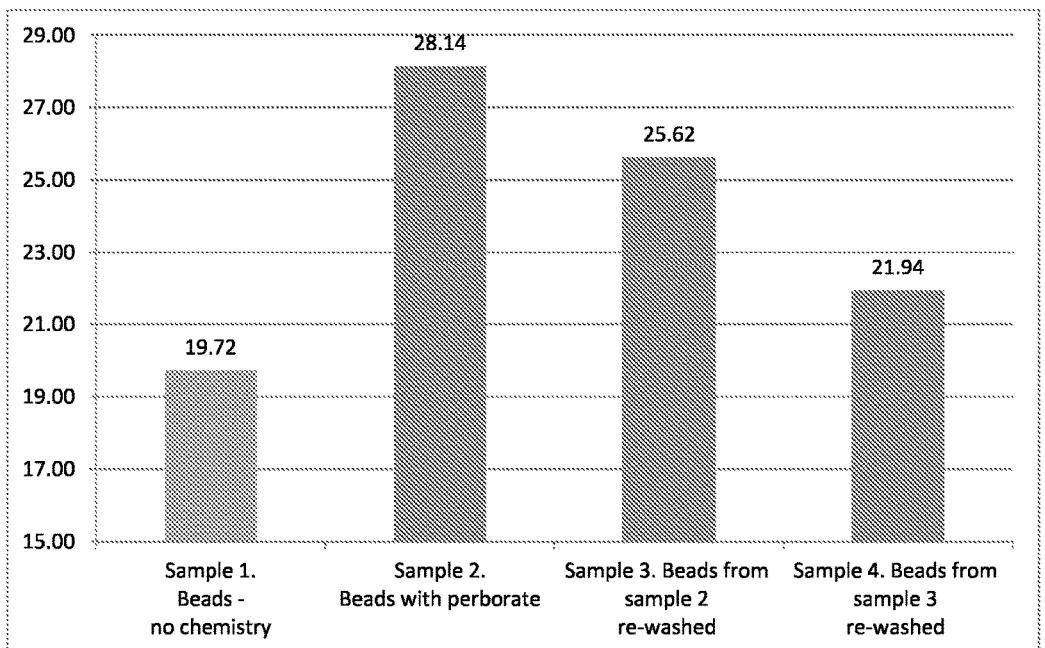
FIGURE 12  BLEACHING WITH SODIUM PERBORATE TREATED BEADS IN THE XEROS® GENERATION 2 PROTOTYPE WASHER EXTRACTOR

CLEANING MATERIAL

FIELD OF THE INVENTION

This invention relates to a novel cleaning material that finds particular application in cleaning processes which operate in the presence of limited quantities of water and use a cleaning formulation which comprises solid polymeric cleaning particles in combination with suitable detergent formulations. Most particularly, the system utilises a cleaning formulation wherein the detergent formulations are immobilised on the solid polymeric cleaning particles.

BACKGROUND TO THE INVENTION

Traditional aqueous cleaning is a process of major importance for textiles which routinely uses large quantities of water in combination with appropriate detergent formulations. These formulations are complex, but typically comprise surfactants, with or without a series of enzymes to provide a biological action in the removal of certain stains, together with oxidising or bleaching components and their associated activators, to neutralise highly coloured stains. In addition, the formulations generally also include builders to control water hardness, anti-redeposition additives to prevent re-settling of removed soil back on to the textile surface, perfumes to ensure a suitable level of fragrancy, and optical brighteners to further mask the effects of redeposition—particularly on white garments.

In conventional aqueous cleaning processes, the detergent formulation is usually added as an all-in-one dosing, or there may be a wash and rinse split, wherein a softener or other formulated additive is added as a separate stage. The problem that arises, however, is that there is a significant dilution of the components in the detergent formulation at the textile surface as the wash cycle progresses, with the consequence that good cleaning occurs at the expense of the removal of anti-redeposition additives, perfumes and optical brighteners from the cleaned textile. These three parts of the detergent formulation, most particularly, are instrumental in meeting consumer needs when cleaning quality is judged. Hence, in conventional aqueous cleaning processes, all-in-one detergent formulations are effectively overloaded with these chemicals, in order to ensure that they remain present in sufficient quantities on the final cleaned textile surface. Naturally, this increases the overall detergent dosage level in the wash and the cost of the detergent formulation itself.

WO-A-2007/128962 discloses a cleaning process that employs a formulation which requires the use of only limited amounts of water, thereby offering significant environmental benefits. Thus, the inventors of WO-A-2007/128962 disclosed a method for cleaning a soiled substrate, the method comprising the treatment of the moistened substrate with a formulation comprising a multiplicity of polymeric particles or beads. Whilst the method of WO-A-2007/128962 can employ similar detergent formulations to traditional aqueous cleaning processes—at significantly reduced dosage levels—there is still an inherent inefficiency to all-in-one dosing.

These difficulties are therefore addressed in WO-A-2011/128680, which describes a modified detergent dosing process for use when cleaning using polymeric beads. In this method, the detergent formulation is split into its constituent chemical parts, with these being added at different times during the cleaning process, specifically during the wash and rinse sections of the cycle. In this way, not only is the overall chemical loading reduced, but the more expensive components of the formulations can be added when they are likely to be most effective for cleaning performance. As a consequence, considerable cost savings are achieved when compared with conventional all-in-one detergents.

The methods disclosed in WO-A-2007/128962 and WO-A-2011/128680 use only a limited amount of water, thereby providing environmental benefits. Whilst there are, therefore, significant advantages over the methods of the prior art, there still remains a difficulty, in that the re-use of the same detergent formulation components over several washes is not possible, thus leading to expensive repeat dosing from wash to wash. Consequently, the present inventors have sought to address this problem by providing a modified cleaning composition wherein detergent components are immobilised on the polymeric beads used in the method of WO-A-2007/128962, thereby providing improved cleaning performance, as well as the ability to re-use these detergent components over multiple washes.

WO-A-2012/104861 relates to the use of a PVC surface co-immobilised with multiple enzymes for the removal of stains which is useful in the field of washing or cleaning household textiles, and provides processes for the preparation and use of the PVC surfaces. It appears that the inventors are concerned only with the treatment and use of PVC surfaces, typically in the form of a container and brush, with formulations comprising multiple enzymes, and do not consider the use of cleaning materials in the form of polymeric beads.

SUMMARY OF THE INVENTION

Thus, according to a first aspect of the present invention, there is provided a cleaning formulation comprising a multiplicity of solid cleaning particles, wherein said solid cleaning particles comprise polymeric particles and at least one cleaning agent, wherein said at least one cleaning agent is immobilised on the surface of said polymeric particles.

Most particularly, said at least one cleaning agent is immobilised on the surface of said polymeric particles by means of chemical bonds.

In certain embodiments of the invention, said chemical bonds comprise ionic bonds.

In alternative embodiments of the invention, said chemical bonds comprise hydrogen bonds.

In further embodiments of the invention, said chemical bonds comprise covalent bonds.

In still further embodiments of the invention, said chemical bonds comprise polar bonds or bonds formed by virtue of unequal charge distributions between polymeric particles and immobilised materials.

In certain embodiments of the invention, immobilisation may be achieved by direct treatment of the polymeric particles with the at least one cleaning agent, such that the at least one cleaning agent is directly bonded to the polymeric particles.

In alternative embodiments of the invention, the polymeric particles may initially be treated with at least one activating agent in order to modify the chemical properties at the surfaces of the polymeric particles; subsequent treatment or reaction of the at least one cleaning agent with the modified particles thereby facilitates immobilisation of the said agent. In said embodiments, the at least one cleaning agent may be bonded to the polymeric particles via a linking group or moiety.

In further embodiments of the invention, the polymeric particles comprise polar groups and said treatment with at least one activating agent comprises treatment with at least one polar group-containing material, such that the at least one polar group-containing material and at least one cleaning agent are applied to said polymeric particles in layers, and said at least one cleaning agent is bonded to the polymeric particles by immobilisation thereon by means of ionic and/or polar bonds and/or other chemical bonds formed by virtue of unequal charge distributions between the polymeric particles and layers of immobilised materials.

Optionally, in said embodiments, said treatment with at least one activating agent and subsequent treatment or reaction with at least one cleaning agent with the modified particles may comprise multiple treatments with the at least one activating agent and/or multiple subsequent treatments or reactions with the at least one cleaning agent.

Solid polymeric cleaning particles may comprise either foamed or unfoamed polymeric materials. Furthermore, the polymeric particles may comprise polymers which are either linear or crosslinked.

Solid polymeric cleaning particles preferably comprise polyalkenes such as polyethylene and polypropylene, polyamides, polyesters or polyurethanes. Typically, however, said polymeric particles comprise polyamide or polyester particles, most particularly particles of nylon, polyethylene terephthalate or polybutylene terephthalate, often in the form of beads. Said polyamides and polyesters are found to be particularly effective for aqueous stain/soil removal, whilst polyalkenes are especially useful for the removal of oil-based stains. Each of said polymeric solid cleaning particles is typically substantially cylindrical or spherical in shape and has an average density in the range of 0.5-2.5 g/cm$^3$ and an average volume in the range of 5-275 mm$^3$.

Optionally, copolymers of the above polymeric materials may be included in said polymeric cleaning particles. Specifically, the properties of the polymeric materials may be tailored to specific requirements by the inclusion of monomeric units which confer particular properties on the copolymer. Thus, the copolymers may be adapted to attract particular staining materials by comprising monomers which, inter alia, are ionically charged, or include polar moieties or unsaturated organic groups.

Said at least one cleaning agent most particularly comprises at least one detergent, which typically comprises at least one surfactant. Said cleaning agents are especially cleaning chemicals which are typically components of the detergent formulation used in a conventional wash process and, therefore, typically comprise surfactants, enzymes, oxidising agents or bleaches.

According to a second aspect of the invention, there is provided a method for the cleaning of a substrate, said method comprising the treatment of the substrate with a formulation according to the first aspect of the invention.

The method of the second aspect of the invention is carried out in an aqueous environment in the presence of limited quantities of water. In other words, the amount of water present during the performance of the method of the invention is far less than in the case of the methods of the prior art, thereby providing one of the principal benefits associated with said method.

According to the method of the second aspect of the present invention, said cleaning agents are delivered directly to the substrate surface by means of controlled, localised application from the polymeric particles containing these agents. In this way the cleaning agents are delivered in the most targeted manner possible, thereby reducing the amount of agent required to achieve the desired cleaning effect. Furthermore, there is no requirement for the use of complex cartridge or other dosage devices, and no need to use additional water to transport the agent to the fabric surface.

Solid cleaning particles are typically added at a particle to substrate addition level of 0.1:1-30:1 by dry mass of substrate (washload).

The substrate treated by the claimed method may comprise any of a wide range of substrates, including, for example, plastics materials, leather, paper, cardboard, metal, glass or wood. In practice, however, said substrate most preferably comprises a textile fibre, which may be either a natural fibre, such as cotton, or a synthetic textile fibre, for example nylon 6,6 or a polyester, or a blend of natural and synthetic fibres.

The wash system provided by the present invention is designed to improve mechanical interaction between all of the particles of the cleaning formulation and the fabrics, and facilitates the easy removal of the solid cleaning particles from the fabrics after the cleaning process is complete. The claimed wash system also facilitates the re-use of the particles of the cleaning formulation in a number of subsequent processes according to the method and, unlike the methods of the prior art, does not necessitate the addition of fresh cleaning agents prior to each re-use according to the method. Furthermore, the invention is not limited to procedures for cleaning fabrics and is applicable to any solid particle cleaning process, such as dish washing or carpet cleaning.

A third aspect of the present invention envisages a method for the preparation of a cleaning formulation according to the first aspect of the invention, said method comprising treating a multiplicity of polymeric particles with at least one cleaning agent.

Optionally, said polymeric particles may initially be treated with at least one activating agent prior to treatment with said at least one cleaning agent.

Optionally, said polymeric particles comprise polymeric particles comprising polar groups and said treatment with least one activating agent comprises treatment with at least one polar group-containing material.

In embodiments of the invention wherein the polymeric particles are directly treated with at the least one cleaning agent, said at least one cleaning agent is typically immobilised on said polymeric particles by means of covalent bonds.

In embodiments of the invention wherein the polymeric particles are initially treated with at least one activating agent, said at least one cleaning agent may be immobilised on said polymeric particles by means of covalent bonds, ionic bonds, hydrogen bonds, polar bonds or bonds formed by virtue of unequal charge distributions between polymeric particles and immobilised materials.

Typically, when said polymeric particles comprise polymeric particles comprising polar groups and said treatment with least one activating agent comprises treatment with at least one polar group-containing material, said at least one cleaning agent is immobilised on said polymeric particles by means of ionic bonds, polar bonds or bonds formed by virtue of unequal charge distributions between polymeric particles and immobilised materials.

Typically, the cleaning formulation according to the invention may be re-used for at least five separate cycles of the cleaning method according to the second aspect of the invention prior to re-treatment of the polymeric particles with at least one cleaning agent according to the method of the third aspect of the invention. The polymeric particles comprised in the formulation may be re-treated in this way several times before significant deterioration in performance is observed and, consequently, can be re-used in the cleaning method of the invention for many washing cycles.

BRIEF DESCRIPTION OF THE DRAWINGS

Embodiments of the invention are further described hereinafter with reference to the accompanying drawings, in which:

FIG. 1 provides an illustration of a WKF Stain Sheet template;

FIG. 2 is a graphical representation of the Cleaning Effect on WKF Stain 11 after Washing at 40° C. with Amylase Treated Beads;

FIG. 3 is a graph illustrating the Amylase Activity observed with Polymer 1/Amylase in Solution and after Treatment of Beads;

FIG. 4 is a graph which shows the Cleaning Effect on WKF Stain 10 after Washing with Borax at 60° C.;

FIG. 5 provides a graphical illustration of the Cleaning Effect achieved on WKF Stain 11 (Starch) when Washed with Beads Treated with Amylase and Perborate;

FIG. 6 is a graphical representation of the Cleaning Effect on WKF Stain 12 after Washing with Beads Treated with Protease;

FIG. 7 shows a graph illustrating the Cleaning Effect on WKF Stain 11 (Starch) when washed with a Formulation comprising Detergent and Beads Treated with Amylase;

FIG. 8 is a graph which illustrates the Cleaning Effect on WKF Stain 11 (Starch) when washed with Beads Treated with Amylase before and after Washing with Surfactant;

FIG. 9 provides a graphical illustration of the Cleaning Effect achieved on WKF Stain 11 after Washing with Beads Treated with Amylase and Lipase;

FIG. 10 provides a graphical illustration of the Cleaning Effect achieved on WKF Stain 5 when Washed with Beads Treated with Amylase and Lipase;

FIG. 11 shows a graph illustrating the results of a Modified Phadebas® Test on Polypropylene Beads when Treated with Amylase; and FIG. 12 graphically illustrates the Effect of Bleaching with Sodium Perborate Treated Beads in a Xeros® Generation 2 Prototype Washer Extractor.

DESCRIPTION OF THE INVENTION

The first aspect of the invention envisages a cleaning formulation as hereinbefore defined, which comprises a multiplicity of solid cleaning particles, wherein said solid cleaning particles comprise polymeric particles and at least one cleaning agent, wherein said at least one cleaning agent is immobilised on the surface of said polymeric particles.

Most particularly, said at least one cleaning agent is immobilised on the surface of said polymeric particles by means of chemical bonds.

In certain embodiments of the invention, said chemical bonds comprise ionic bonds.

In alternative embodiments of the invention, said chemical bonds comprise hydrogen bonds.

In further embodiments of the invention, said chemical bonds comprise covalent bonds.

In still further embodiments of the invention, said chemical bonds comprise polar bonds or bonds formed by virtue of unequal charge distributions between polymeric particles and immobilised materials.

Typically, the cleaning agents comprise surfactants, enzymes, oxidising agents or bleaches.

In certain embodiments of the invention immobilisation may be achieved by direct treatment of the polymeric particles with the at least one cleaning agent. Such embodiments include, for example, the treatment of Nylon 6,6 particles with a bleaching agent such as borax decahydrate.

In alternative embodiments of the invention the polymeric particles are initially treated with at least one activating agent in order to modify the chemical properties at the surfaces of the polymeric particles in order that the modified particles may subsequently be treated with at least one cleaning agent in order to facilitate immobilisation of the said agent.

In certain embodiments the activated polymer particle is then further treated with a linking agent which facilitates attachment of the cleaning agent by means of a covalent bond. Said embodiments may include, for example, the treatment of Nylon 6,6 particles initially with sodium perborate tetrahydrate in order to partially hydrolyse the bead surface. The activated surface may then be treated with a suitable linking agent, such as glutaraldehyde, which provide linking groups which facilitate the immobilisation on the particle surface of a range of enzymes including, for example, lipase, protease or an amylase, such as Stainzyme®.

Activating agents which may be used to provide reactive moieties on the surface in this way, and thereby to facilitate attachment of cleaning agents include, in certain embodiments of the invention, chemical agents such as enzymes, oxidising agents or bleaches. It will be appreciated that such agents are themselves useful as cleaning agents and that suitable examples of such materials are therefore detailed elsewhere in this document. Thus, a polymer particle may be subjected to a first treatment with an activating agent under a first set of conditions and the activated polymer particle can then be subjected to a second treatment with a cleaning agent under a second set of conditions. The activating agent and the cleaning agent may be the same or different materials and the treatments may be carried out in the same apparatus and at similar temperatures.

In other embodiments of the invention, activation of the surface may be achieved by the use of physical agents, such as heat or electromagnetic radiation, e.g. ultra-violet radiation or microwave radiation prior to reaction with a linking agent.

Suitable linking agents may, as indicated above, include glutaraldehyde, or may be selected from, for example, typical crosslinking agents such as dimethyl adipimidate, dimethyl suberimidate, pentafluorophenyl ester, hydroxymethyl phosphine, imidoesters and N-hydroxysuccinimide esters.

Other suitable linking agents include, for example:
N-Hydroxysuccinimide (NHS) and N-(3-Dimethylaminopropyl)-N'-ethylcarbodiimide hydrochloride (EDC);
Acylimidazoles (e.g. Carbonyl Diimidazole (CDI) and N,N'-carbonylbis(3-methylimidazolium)triflate (CBMIT);
Phosphonium salts (e.g. benzotriazol-1-yl-oxy-tris-(dimethylamino)-phosphonium hexafluorophosphate (BOP);
Uronium salts (e.g. O-((ethoxycarbonyl)cyanomethyleneamino)-N,N,N',N'-tetramethyl-uronium tetrafluoroborate (TOTU); and
Mukaiyama's reagent (2-chloro-1-methylpyridinium iodide).

Alternatively, embodiments utilising activating agents may include the treatment of polymeric particles incorporating polar groups, including for example Nylon 6,6 or poly(ethylene terephthalate), initially with a polar group-containing material—such as, for example, gelatin, starch, cellulose, chitosan, chitan, carboxymethylcellulose, poly (vinylimidazoles), poly(acrylic acid), poly(methacrylic acid), poly(lactic acid), poly(maleic acid), poly(glycolic acid), poly(acrylonitrile), poly(vinylpyrrolidone), poly(dimethylaminoethyl methacrylate), poly(ethylene imine), poly(allylamine), poly(allylamine) hydrochloride, poly(ethylene glycol), poly(propylene glycol), poly(acrylamide), poly(vinyl alcohol), poly(vinyl acetate), poly(vinyl formamide), poly(vinylamine), amine-containing molecules (including biomolecules such as proteins), carboxylic acids such as maleic acid and itaconic acid, and carboxylic acid-containing polymers, as well as derivatives and copolymers of all the foregoing—wherein ionic interactions are formed between the polymer particles and a layer of the polar group-containing material, and subsequently with cleaning agents, such as enzymes—including, for example, lipase, protease or an amylase such as Stainzyme®—wherein further ionic interactions are established between the layer of polar group-containing material and the layer of cleaning agent.

Optionally, said embodiments utilising at least one activating agent may comprise multiple treatments with the at least one activating agent and/or multiple subsequent treatments or reactions with the at least one cleaning agent. Said embodiments, which rely on ionic interactions, do not require the use of a linker.

The cleaning agents may optionally also include, for example, builders, chelating agents, dye transfer inhibiting agents, dispersants, enzyme stabilizers, catalytic materials, bleach activators, polymeric dispersing agents, clay soil removal agents and suds suppressors.

Examples of suitable surfactants may be selected from non-ionic and/or anionic and/or cationic surfactants and/or ampholytic and/or zwitterionic and/or semi-polar nonionic surfactants. The surfactant is typically present at a level of from about 0.1%, from about 1%, or even from about 5% w/w of the particle mass up to about 99.9%, to about 80%, to about 35%, or even to about 30% w/w of the particle mass, or any of the ranges defined thereby.

Examples of suitable enzymes include, but are not limited to, hemicellulases, peroxidases, proteases, other cellulases, other xylanases, lipases, phospholipases, esterases, cutinases, pectinases, keratanases, reductases, oxidases, phenoloxidases, lipoxygenases, ligninases, pullulanases, tannases, pentosanases, malanases, [beta]-glucanases, arabinosidases, hyaluronidase, chondroitinase, laccase, mannanase and amylases, or mixtures thereof. A typical combination may comprise a mixture of enzymes such as protease, lipase, cutinase and/or cellulase in conjunction with amylase.

Optionally, enzyme stabilisers may also be included amongst the cleaning agents. In this regard, enzymes for use in detergents may be stabilised by various techniques, for example by the incorporation of water-soluble sources of calcium and/or magnesium ions in the compositions.

Examples of suitable bleach compounds include, but are not limited to, borax decahydrate, peroxygen compounds, including hydrogen peroxide, inorganic peroxy salts, such as perborate, percarbonate, perphosphate, persilicate, and mono persulphate salts (e.g. sodium perborate tetrahydrate and sodium percarbonate), and organic peroxy acids such as peracetic acid, monoperoxyphthalic acid, diperoxydodecanedioic acid, N,N'-terephthaloyl-di(6-aminoperoxycaproic acid), N,N'-phthaloylaminoperoxycaproic acid and amidoperoxyacid. Bleach activators include, but are not limited to, carboxylic acid esters such as tetraacetylethylenediamine and sodium nonanoyloxybenzene sulfonate.

Suitable builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxybenzene-2,4,6-trisulphonic acid, and carboxymethyl-oxy-succinic acid, various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

One or more copper, iron and/or manganese chelating agents and/or one or more dye transfer inhibiting agents may also be included. Suitable dye transfer inhibiting agents include polyvinylpyrrolidone polymers, polyamine N-oxide polymers, copolymers of N-vinylpyrrolidone and N-vinylimidazole, polyvinyloxazolidones and polyvinylimidazoles, or mixtures thereof.

The cleaning agents can also optionally contain dispersants. Suitable water-soluble organic dispersants are homo- or co-polymeric polycarboxylic acids, or their salts, in which the polycarboxylic acid may comprise at least two carboxyl radicals separated from each other by not more than two carbon atoms.

The solid cleaning particles are of such a shape and size as to allow for good flowability and intimate contact with a soiled substrate, which typically comprises a textile fabric. In the context of the present invention, therefore, said particles typically comprise cylindrical or spherical beads. It is found that the combination of particle size, shape and density is such that the mechanical interaction of the particle with the fabric is optimised, it being sufficiently vigorous to provide effective cleaning but, at the same time, uniform and gentle enough to reduce fabric damage when compared with conventional aqueous processes. It is, in particular, the uniformity of the mechanical action generated by the chosen particles across the entire fabric surface that is the key factor in this regard. Such uniform mechanical action is also the key to localised and controlled application of the cleaning agents from the polymeric particles across the entire substrate surface.

The particle parameters are also controlled so as to allow for easy separation of the particles from the washload at the end of the wash process. Thus, particle size and shape may be controlled in order to minimise entanglement with the substrate, and the combination of suitable particle density and high free volume (ullage) in the washing machine tumbling process together promote particle removal. This is especially relevant in the case of fabric treatment processes.

In the method according to the second aspect of the invention, the ratio of solid cleaning particles to substrate is generally in the range of from 30:1 to 0.1:1 w/w (dry mass of substrate (washload)), preferably in the region of from 10:1 to 1:1 w/w, with particularly favourable results being achieved with a ratio of between 5:1 and 1:1 w/w, and most particularly at around 2:1 w/w. Thus, for example, for the cleaning of 5 g of fabric, 10 g of solid cleaning particles would be employed.

In order to provide additional lubrication to the system, and thereby improve the transport properties within the system, water is added to the system. Optionally, a soiled substrate may be moistened by wetting with mains or tap water prior to loading into a cleaning apparatus. In any event, water is added to the process such that the washing treatment is carried out so as to achieve a water to substrate ratio which is typically between 2.5:1 and 0.1:1 w/w; more frequently, the ratio is between 2.0:1 and 0.8:1, with particularly favourable results having been achieved at ratios such as 1.5:1, 1.2:1 and 1.1:1.

As previously noted, the method of the invention finds particular application in the cleaning of textile fibres and fabrics. The conditions employed in such a cleaning system are very much in line with those which apply to the conventional wet cleaning of textile fibres and, as a consequence, are generally determined by the nature of the fabric and the degree of soiling. Thus, typical procedures and conditions are in accordance with those which are well known to those skilled in the art, with fabrics generally being treated according to the method of the invention at, for example, temperatures of between 5 and 95° C. for a duration of between 10 minutes and 1 hour, then being rinsed in water and dried. The release of cleaning agents from the cleaning particles is controlled such that these release over a series of washes.

The localised delivery of cleaning agents to the fabric surface by the cleaning particles is the predominant feature that ensures excellent cleaning performance. No problems are observed with solid cleaning particles adhering to the fibres at the conclusion of the cleaning operation, and all particles may subsequently be removed from the substrate of the washload. The method of the invention may particularly advantageously be carried out by using, for example, cleaning apparatus as disclosed in WO-A-2010/094959, WO-A-2011/064581 and WO-A-2011/098815.

The method of the second aspect of the present invention may be used for either small or large scale batchwise processes, and it finds application in both domestic and industrial cleaning processes. The method also find application in continuous processes, and in processes which combine batchwise and continuous operations.

The method of the second aspect of the invention may be applied to the cleaning of any of a wide range of substrates including, for example, plastics materials, leather, paper, cardboard, metal, glass or wood. In practice, however, said method is principally applied to the cleaning of substrates comprising textile fibres and fabrics, and has been shown to be particularly successful in achieving efficient cleaning of textile fabrics which may, for example, comprise either natural fibres, such as cotton, or man-made and synthetic textile fibres, for example nylon 6,6, polyester, cellulose acetate, or fibre blends thereof.

The conditions employed in such cleaning systems when applied to textile fabrics do, however, allow the use of surprisingly lower wash temperatures from those which typically apply to the conventional wet cleaning of textile fabrics and, as a consequence, offer significant environmental and economic benefits.

Additionally, as previously noted, re-utilisation of the solid cleaning particles is facilitated without the necessity for the addition of fresh cleaning agent in each subsequent washing procedure according to the method. Re-treatment of the polymeric particles with cleaning agent is, however, desirable after a number of washing cycles, and the polymeric particles may be retreated in this way, and re-used in the method of the second aspect of the invention in a multiplicity of washing cycles.

The method of the third aspect of the invention may optionally be performed using the cleaning apparatus disclosed in WO-A-2010/094959, WO-A-2011/064581 and WO-A-2011/098815, by circulating the polymeric particles and the cleaning agent in the absence of any soiled substrate. This approach is particularly advantageous for the re-treatment of previously used polymeric particles, as it avoids the requirement for the removal of the particles from the apparatus between cleaning cycles according to the method of the second aspect of the invention.

In certain embodiments, the method of the third aspect of the invention may be carried out at elevated temperatures, typically between 5° and 100° C., with favourable results being achieved with the immobilisation of enzymes on polymeric particles in the range of 20-40° C., whilst the immobilisation of bleaches is typically effected at temperatures of around 50-100° C. Typically in said embodiments immobilisation of the cleaning agent is achieved by means of the formation of chemical bonds which comprise covalent bonds.

In alternative embodiments of the invention, method of the third aspect of the invention may be carried out at ambient temperatures, typically between 15° and 30° C., with favourable results being achieved with the immobilisation of enzymes and bleaches on polymeric particles in the range of 20-25° C. Typically in said embodiments immobilisation of the cleaning agent is achieved by means of the formation of ionic or polar bonds or other chemical bonds formed by virtue of unequal charge distributions between polymeric particles and immobilised materials.

The invention will now be further illustrated, though without in any way limiting the scope thereof, by reference to the following examples.

EXAMPLES

Example 1

Bleaching

Nylon 6,6 beads (6.0 kg of Rhodia Technyl XA1493—these beads were used in each Example) were added to a continuously stirred reaction vessel, and treated with borax decahydrate (60.0 g) dissolved in water (9.0 kg) at 65-70° C. for 60 minutes. The beads were then sieved out from this mixture, and rinsed with water (12.0 kg) at ambient temperature to remove residual unreacted borax decahydrate. These beads were then re-used without any added detergency in a number of fabric washing cycles (each with 3.0 kg of cotton ballast and 7.2 kg of water at 40-45° C. for 60 minutes) as shown in Table 1. A horizontal axis, sealed rotating drum adapted with a single agitator (or lifter) was used for this purpose (drum volume 137 litres). The beads were then removed and rinsed with 6.0 kg of water at ambient temperature between each wash cycle. Three WFK stain monitors (PCMS-55_05-05x05, as illustrated in FIG. 1) were used to assess cleaning performance, and three sebum sheets (WFK SBL2004) added to provide a significant further soil loading. Measurements of the CIE L*, a* and b* colour parameters were made for each bleachable stain type on these stain monitors, using a Konica-Minolta CM-3600A spectrophotometer (UV component included, 8° aperture). The bleachable stains tested were:

Red wine on Cotton, aged (IEC456);
Curry on Cotton;
Blood on Cotton, aged (IEC456); and
Pigment/Vegetable Fat/Milk on Cotton.

The dE colour changes were then calculated for these stains versus their equivalents on unwashed stain monitors used as controls (higher values of dE reflecting better cleaning performance). These dE values were then averaged across all of these stains to give an overall measure of bleaching performance. It should be noted that a high level of cleaning performance will only be achieved when bleaching chemistry is active in the cleaning formulation—in this case on the surface of the polymer beads.

TABLE 1

BLEACHING EFFECT FROM BORAX DECAHYDRATE MODIFIED NYLON BEADS

| Bead Sample | Average dE for Bleachable Stain Cleaning |
|---|---|
| Unmodified nylon polymer (control) | 18.78 |
| Borax decahydrate modified polymer: Wash #1 | 28.41 |
| Borax decahydrate modified polymer: Wash #2 | 21.77 |
| Borax decahydrate modified polymer: Wash #3 | 21.49 |
| Borax decahydrate modified polymer: Wash #4 | 20.74 |
| Borax decahydrate modified polymer: Wash #5 | 19.11 |
| Borax decahydrate modified polymer: Wash #6 | 18.78 |

As can be seen from Table 1, the bleaching performance of the borax decahydrate modified Nylon 6,6 beads is significantly improved versus the unmodified bead control. Furthermore, this bleaching effect remains superior to the control (higher dE) for the following 5 washes, without any added detergency in the system.

Example 2

Enzymatic Cleaning

Two restrictions hamper the reaction of enzymes with Nylon 6,6—the absence of strongly reactive groups in the polymer, and its weak polar surface. In order to overcome these deficiencies, the present inventors have developed a novel reaction scheme to attach enzymes onto nylon. This first involves the treatment of the nylon with a bleaching or oxidising agent, such as sodium perborate tetrahydrate, which partially hydrolyses the bead surface. Following this treatment, a subsequent treatment with glutaraldehyde provides reactive moeities for subsequent combination with an enzyme (e.g. Stainzyme®—an amylase produced by Novozymes). This process has the additional benefit of incorporating some bleaching agent onto the nylon—as there is not generally 100% stoichiometric reaction of the enzyme. This is a secondary effect, but one which nonetheless could be carefully controlled to combine both enzymes and oxidising bleach chemistry in a stable state within the same detergent composition. Overall, the reaction chemistry here is simpler, cheaper and more effective than previously proposed enzyme immobilisation schemes.

In this example, nylon beads (5.6 kg of Rhodia Technyl XA1493) were added to a continuously stirred reaction vessel, and then treated with sodium perborate tetrahydrate (60.0 g) dissolved in water (6.0 kg) at 65-70° C. for 60 minutes. The beads were cooled to ambient temperature, and a further 3.0 kg of water added, before treatment with glutaraldehyde (312.4 g), stirred in at ambient temperature for 60 minutes. The beads were then sieved out from this mixture, and washed with 12.0 kg of potassium phosphate solution (0.1M, pH 7.5) to remove any excess glutaraldehyde. The beads were subsequently rinsed with a further 12.0 kg of water at ambient temperature and returned in a damp condition to the reaction vessel. Stainzyme® 12 L (ex Novozymes) (360 g) was added to the beads in 3.0 kg water, and this mixture was stirred at ambient temperature for a further 2 hours. Finally, the treated beads were sieved and again rinsed with 12.0 kg of water at ambient temperature, to remove residual unreacted chemicals on their surface.

These beads were then re-used without any added detergency in a number of fabric washing cycles (each with 3.0 kg of cotton ballast, 7.2 kg of water at 40-45° C., for 60 minutes) as shown in Table 2. A horizontal axis, sealed rotating drum adapted with a single agitator (or lifter) was used for this purpose (drum volume 137 litres). The beads were removed and rinsed with 6.0 kg of water at ambient temperature between each wash cycle. Three WFK stain monitors (PCMS-55_05-05x05) were used to assess cleaning performance. Measurements of the CIE L*, a* and b* colour parameters were made for the amylase enzymatic stain type: starch/pigment on cotton, using a Konica-Minolta CM-3600A spectrophotometer (UV component included, 8° aperture). The dE colour changes were then calculated for this stain versus its equivalent on unwashed stain monitors used as controls (higher values of dE again reflecting better cleaning performance). These dE values were then averaged for this stain to give an effective measure of cleaning performance. A high level of cleaning performance will only be achieved when amylase is active in the cleaning formulation—in this case on the surface of the polymer beads.

As can be seen from Table 2, the cleaning performance of the amylase modified beads is significantly improved versus the unmodified nylon 6,6 bead control.

TABLE 2

ENZYMATIC CLEANING EFFECT FROM AMYLASE MODIFIED NYLON BEADS

| Sample | Average dE for Starch Stain Cleaning (Amylase Activity) |
|---|---|
| Unmodified Nylon | 5.68 |
| Amylase Immobilised Nylon Beads First Wash | 10.74 |
| Amylase Immobilised Nylon Beads Second Wash | 11.41 |
| Amylase Immobilised Nylon Beads Third Wash | 11.45 |
| Amylase Immobilised Nylon Beads Fourth Wash | 10.86 |
| Amylase Immobilised Nylon Beads Fifth Wash | 8.94 |

Furthermore, the results clearly show this improvement is maintained for at least 5 wash cycles, demonstrating sustained increased amylase activity compared to the control.

Example 3

Enzymatic Cleaning

This example illustrates the cleaning effect achieved when using Nylon 6,6 cleaning beads which have been modified by the covalent immobilisation thereon of amylase. Amylase is attached to the polymeric particles by chemical reactions, using relatively high temperatures and high concentrations of chemicals, as detailed below. The polymeric particles comprising immobilised amylase were then evaluated in a simulated domestic wash for three consecutive cycles at 20° C. and 40° C.

2 kg of Nylon 6,6 beads (Rhodia Technyl XA1493) were treated with borax, glutaraldehyde and amylase as follows:

1. Borax Treatment to Hydrolyse the Surface of the Nylon Bead:

150 g of sodium borate decahydrate (Borax) was added to the 2 kg of unmodified nylon beads in a thick plastic bag with 2 L of hot water (88-100° C.). This sealed bag was rotated in a horizontal axis sealed rotating drum apparatus adapted with a single agitator (lifter) for 3 hours at 15 rpm before being rinsed in tap water at approximately 9-15° C.

2. Treatment with Glutaraldehyde which Acts as a Cross-linking Agent to Bridge the Borax to Amylase.

120 g of glutaraldehyde was added to the Borax modified beads with 2 L of cold tap water and spun for 1 hour at 15 rpm in the horizontal axis sealed rotating drum apparatus adapted with a single agitator (lifter) at room temperature before being rinsed in cold tap water.

3. Amylase Treatment:

100 g of Stainzyme Plus® solution was added to same beads as above with 2 L of tap water and spun in the horizontal axis sealed rotating drum apparatus adapted with a single agitator (lifter) for 1 hour at 15 rpm at room temperature before being rinsed with tap water. The chemistry used in this example to treat the beads is in a large excess to ensure there is enough agent at each stage to allow the agent at the next stage to be attached in order to show an enzymatic cleaning effect of amylase on the stains.

The treated beads were then washed in a sealed plastic bag (to prevent contamination) with a 1 kg wash load including 1 sebum sheet and 1 WFK stain sheet and 2 L of tap water at 20° C. The bag was spun in the horizontal axis sealed rotating drum apparatus adapted with a single agitator (lifter) for 30 minutes at 50 rpm, changing direction every 5 minutes. The load was then put into a rinse and spin cycle in a washing machine (Beko, WM5120W 5 Kg) (1200 rpm) and the stain sheet was analysed on the Konica Minolta CM-3600A spectrophotometer with SpectraMagic NX software (UV component included, 8° aperture). Samples of beads and the wash liquor were taken after each test and these were then tested for the presence of active amylase using an adapted method of the Phadebas® Amylase tests, as described below.

This technique was repeated at temperatures of 20° and 40° C. with separate batches of nylon beads, and each series of tests was completed within one week. The water used was heated to the same approximate temperature as the temperature of the horizontal axis sealed rotating drum apparatus adapted with a single agitator (lifter). All temperatures were recorded before and after the test cycle, i.e. water, machine and room temperature. Controls were with and without untreated beads were also carried out under the same methodology.

As shown in FIG. 1, a WFK stain sheet consists of 13 stains plus an area of measurement (14) for redeposition of soil onto the cloth itself. The washed stain sheets are compared to unwashed stain sheets and the colour change (dE) is measured; the higher dE, the better the cleaning performance, and one dE difference is visible to the eye.

The selection of stains on the stain sheet aims to simulate stains commonly found in a household and each of numbers 1-13 represents a stain. The number on the sheet is the batch number and is the position where the test code is written before being tested/washed. The stains and the effects they are designed to show or react to are as follows:

| Number | Stain | Designed to Test |
|---|---|---|
| 1 | Pigment/Lanolin on Cotton | General Detergency |
| 2 | Pigment/Lanolin on Polyester/Cotton | General Detergency |
| 3 | Red wine on Cotton, aged (IEC456) | Bleach |
| 4 | Pigment/Sebum on Cotton | General Detergency |
| 5 | Pigment/Sebum on Polyester/Cotton | General Detergency |
| 6 | Curry on Cotton | Bleach, Amylase |
| 7 | Motor Oil/Pigment on Cotton | General Detergency |
| 8 | Soot/Mineral oil on Cotton (IEC456) | General Detergency |
| 9 | Blood on Cotton, aged (IEC456) | Bleach, Protease |
| 10 | Egg/Pigment on Cotton | General Detergency, Protease |
| 11 | Starch/Pigment on Cotton | General Detergency, Amylase |
| 12 | Pigment/Vegetable Fat/Milk on Cotton | Bleach, Amylase, Protease |
| 13 | Cocoa on Cotton, aged (IEC456) | General Detergency, Protease |
| 14 | Redeposition onto Cloth | Redeposition |

As previously discussed, the presence of active amylase is measured using an adapted method of the Phadebas® Amylase test. The adapted methodology of the Phadebas test consists of adding a tablet of starch-blue dye to 10 ml or 10 g of the solution or beads, respectively, plus 10 ml of de-ionised water that has been acclimatised to 37° C. The mixture is then incubated for 15 minutes at 37° C. and the reaction is stopped by adding 1 ml of 0.5 M NaOH solution. The solution is allowed to cool down and settle, and then a 6 ml sample of the supernatant is diluted 1:2 in deionised water and measured using the Konica Minolta CM-3600A spectrophotometer with SpectraMagic NX software.

The results for the tests carried out at 20° C. are shown in Table 3 in respect of the starch stain (stain 11) and the overall effect.

TABLE 3

CLEANING EFFECT OF AMYLASE TREATED BEADS AT 20° C.

| Sample | Overall Amylase Effect/dE | Amylase effect on Starch (stain 11)/dE |
|---|---|---|
| Water - no beads | 3.72 | 3.44 |
| Water - untreated beads | 3.83 | 3.34 |
| Amylase solution - untreated beads | 6.49 | 10.84 |
| Treated beads Wash 1 | 6.75 | 11.72 |
| Treated beads Wash 2 | 5.65 | 8.80 |
| Treated beads Wash 3 | 5.31 | 7.74 |

Considering the amylase effect on the starch stain, it is seen that there is a difference of 8 dE between untreated beads and the beads treated with amylase, suggesting that active amylase has been successfully attached to the bead and that the effect remains after at least three washes.

The overall amylase effect is an average of all the stains that are affected by the presence of amylase, specifically stains 6, 11 and 12, where a 3 dE increase in cleaning performance of the treated beads to untreated beads is still evident.

When the tests were carried out at 40° C., the results for stain 11 showed the presence of amylase over at least three washes, starting with a higher cleaning performance than untreated beads with amylase in solution. This effect is illustrated in FIG. 2.

In both cases, at temperatures of 20° and 40° C., the amylase activity on starch is still seen to be higher after four washes than with untreated beads. Also, the activity of the first wash of amylase treated beads is higher than amylase in solution with untreated beads.

Example 4

Enzymatic Cleaning

This example illustrates the cleaning effect achieved when using Nylon 6,6 cleaning beads which have been modified by the immobilisation thereon of amylase by means of ionic or polar bonds or other chemical bonds formed by virtue of unequal charge distributions between polymeric particles and immobilised materials. The amylase is immobilised by stacking up polymer layers with a total of two layers of amylase. It is found that this method required low concentrations of chemicals when compared to Example 3, and the treatment of the beads was carried out at room temperature. The treated beads were shown to have a positive effect on a simulated domestic wash for three consecutive washes when trials were carried out at 20° C.

It is found that chemicals can be attached and stacked on top of each other on the surface of the beads, using a layer by layer approach. The stacking of positive and negative molecules increases the surface area of the bead and allows more active sites for amylase to attach itself. Hence, amylase was attached onto the surface of nylon 6,6 beads by making use of the differing electrical polarities and thereby generating alternate layers of amylase and "polymer 1" (which was obtained by mixing 1 mg/ml of a poly(acrylic acid) solution (obtained from Alfa Aesar as a 25% solution in water) in phosphate buffer at pH 7.4).

Thus, layers of polymer 1 and amylase were alternately immobilised on the surface of Nylon 6,6 applying the solution of polymer 1 in conjunction with 1 mg/ml of amylase solution in PBS (pH 7.4).

Treatment of the beads was carried out by initially incubating 2 kg of nylon 6,6 beads for two hours at room temperature (approx. 13-23° C.) in 1.5 l of polymer 2 solution so as to form layer 1. The beads were then rinsed thoroughly in running tap water before being incubated for two hours at room temperature in 1.5 l of amylase solution to form layer 2. The beads were again rinsed in tap water before repeating the processes for the application of layers one and two. Hence, four layers were applied to the nylon beads, with the final configuration of the layers being: polymer 2-amylase-polymer 2-amylase. This method of attachment of enzyme to the beads was found to require lower temperatures and lower excesses of treatment chemicals than with direct covalent bonding of the chemicals to the beads.

The treated beads were then added to 1 kg of ballast including 1 sebum and 1 stain sheet as for the procedure of Example 3. The sealed bag was loaded into a horizontal axis sealed rotating drum apparatus adapted with a single agitator (lifter) and cycled for 30 minutes at 20° C. The start temperature of the water, the machine and ambient temperature was measured as well as the temperature of the machine, ballast and room at the end of the procedure.

As a separate test, the same amounts of solutions of polymer 1 and amylase were mixed in a beaker in the same order as above (i.e. as for the application of the two layers of each substance) and the resultant solution was tested for the presence of enzyme activity by using a Phadebas® test. This solution was then added to nylon beads and left to interact for 2 hours, before the beads were rinsed with cold tap water. The beads were then cycled in the horizontal axis sealed rotating drum apparatus adapted with a single agitator (lifter) under the same conditions as above and the stain sheets were measured on the spectrophotometer.

The results showed that, as for the beads in Example 3, the dE of the starch stain (stain 11) increased dramatically when the stain sheet was washed with the beads which were treated with layers of polymer 1 and amylase, as shown in Table 4.

TABLE 4

CLEANING EFFECT OF AMYLASE/POLYMER 1 TREATED BEADS

| Sample | Stain 11 - Starch | Overall Amylase |
|---|---|---|
| Untreated beads | 4.14 | 4.12 |
| Treated beads run 1 | 11.23 | 6.83 |
| Treated beads run 2 | 8.10 | 5.42 |
| Treated beads run 3 | 6.39 | 4.61 |

It was also found that when polymer 1 was mixed in solution with amylase it showed no amylase activity. However, when the solution was added to nylon beads as described above, the beads showed active amylase when tested by the adapted Phadebas® test.

The degree of activity is shown in FIG. 3, wherein the activity of 1 mg/ml amylase solution by itself is seen in the first column, to the left of the chart ($b^*=61.2$); the number represents the blueness of the sample. The activity of a solution of polymer 1 and amylase prepared in a tube in the absence of beads is shown as the second column, and this solution clearly demonstrates no amylase activity ($b^*=0.32$). Addition of this solution to beads and testing of these beads gave the results shown in column three, which demonstrates that significant amylase activity is present, indeed at a higher level than for the amylase solution by itself ($b^*=63.4$). The activity of beads treated with layers of polymer 1 and amylase is shown in column 4 ($b^*=65.4$).

Wash data from stain sheets after wash tests with untreated beads and with beads treated with the polymer 1/amylase solution are shown in Table 5 and clearly illustrate the uplift in cleaning performance of the starch stain (stain 11) which is achieved.

TABLE 5

STARCH STAIN TEST RESULTS AFTER WASHING WITH BEADS SOAKED IN POLYMER 1/AMYLASE SOLUTION

| Sample | Stain 11/dE |
|---|---|
| Untreated beads | 4.14 |
| Beads after soaking in solution of polymer 2 and amylase | 8.92 |

Example 5

Bleaching/Enzymatic Cleaning

This example illustrates the cleaning effect achieved when using Nylon 6,6 cleaning beads which have been modified in three distinct ways. Firstly, beads were treated with borax at high temperature for three hours, as in the first stage of the covalent immobilisation method of Example 3. The second test involved the treatment of beads by an ionic/polar bond layering with a layer configuration of "polymer 1"+"polymer 2"+bleaching agent, where polymer 1 was as described in Example 4, whilst polymer 2 was obtained by mixing a 1 mg/ml solution of poy(ethylene imine) obtained from Alfa Aesar as a 30% w/v solution. One batch was produced using sodium percarbonate as the bleaching agent whilst another batch was produced with sodium perborate. The third test was directed to a combined bleaching/enzymatic cleaning effect and related to a batch of beads treated with sodium perborate (bleaching agent) and amylase. All these examples appeared to have an effect on bleaching stains and the third test also showed an effect on the selected amylase monitor (stain 11).

Thus, for the first test, without being bound by theory, it is believed that borax reacted with the surface of the bead in order to give a bleaching effect without adding additional bleach. The beads were treated using the method described in Example 3 for the borax attachment to the beads, but the remaining steps of that method, i.e. glutaraldehyde and amylase attachment, were not relevant to this example. The optimum temperature for bleaching treatments using borax is considered to be 60° C. so the modified borax beads were tested at 60° C. under standard test conditions as described in Example 3. In this case, the 2 L of water added to the wash was heated to the same temperature, i.e., 60° C.

In order to show that a range of bleaching agents and methods could be used, the second test involved treatment of beads with sodium perborate tetrahydrate (perborate), and subsequent washing was carried out under standard test conditions in a horizontal axis sealed rotating drum apparatus adapted with a single agitator (lifter) at 40° C. for 30 minutes.

According to the third test, one 2 kg batch of nylon beads was treated by the layering method with a configuration of polymer 1+amylase+sodium perborate, and the treated beads were then cycled in the horizontal axis sealed rotating drum apparatus adapted with a single agitator (lifter) for 30 minutes at 40° C. with 1 kg of ballast and 2 litres of 40° C. water.

The first test (borax washing test) at 60° C. showed an improvement in stain 10 (egg/pigment) on the WFK stain sheets that remained for at least three washes, as shown in FIG. 4.

The WFK standard stain sheets include four bleachable stains, these being red wine (stain 3), curry (stain 6), blood (stain 9) and vegetable fat and milk (stain 12). Of particular interest is the curry stain as it clearly shows the effect of bleaching agents present on the beads by producing a 3 to 4 dE increase. As can be seen from Table 6, an initial 3 dE increase in cleaning performance is observed in a washing procedure when using sodium percarbonate treated beads when compared to a washing procedure carried out at the same temperature with beads which are untreated.

It is seen from Table 7 that the use of sodium perborate instead of sodium percarbonate provides an additional uplift of 1 dE in cleaning performance.

TABLE 6

CLEANING PERFORMANCE USING SODIUM PERCARBONATE BLEACH

| Sample - Sodium Percarbonate | Stain 6/dE |
|---|---|
| 40° C. no beads, no chemistry | 0.90 |
| 40° C. untreated beads, no chemistry | 0.74 |
| Sodium Percarbonate run 1 | 3.04 |
| Sodium Percarbonate run 2 | 1.80 |

TABLE 7

CLEANING PERFORMANCE USING SODIUM PERBORATE BLEACH

| Sample - Sodium Perborate | Stain 6/dE |
|---|---|
| 40° C. no beads, no chemistry | 0.90 |
| 40° C. untreated beads, no chemistry | 0.74 |
| Sodium Perborate run 1 | 4.17 |
| Sodium Perborate run 2 | 2.14 |

In test 3, where amylase and sodium perborate were added to the same batch of beads in order to see both a bleaching and an enzymatic effect when washing, it was seen that cleaning of curry stain (stain 6) increased by 3 dE, showing a definite bleaching effect, as can be seen from Table 8.

TABLE 8

CLEANING PERFORMANCE USING SODIUM PERBORATE/AMYLASE

| Sample | Stain 6/dE |
|---|---|
| 40° C. no beads, no chemistry | 0.90 |
| 40° C. untreated beads, no chemistry | 0.74 |
| Amylase + sodium perborate run 1 | 3.22 |
| Amylase + sodium perborate run 2 | 2.6 |

For active amylase, stain 11 is of particular interest and, as shown in FIG. 5, it is apparent that the cleaning performance of the starch stain still improves when washed with treated beads when compared with untreated beads.

Example 6

Enzymatic Cleaning

This example compared the performance of three different enzymes (amylase (Stainzyme® Plus 12L), lipase (Lipex® 100L) and protease (Savinase® Ultra 16XL)—all solutions obtained from Novozymes) when immobilised on nylon 6,6 beads using the ionic/polar bond layering methodology in a simulated wash. Thus, three batches of beads were treated according to the approach adopted in Example 4, but each with only one layer each of polymer 1 and enzyme (as opposed to two layers of each, as in Example 4). When tested, all three batches showed an effect on selected bleachable stains, although it was observed that the beads treated with two layers of amylase had a higher effect than the batch prepared with one layer.

The treated beads were subsequently washed in the horizontal axis sealed rotating drum apparatus adapted with a single agitator (lifter) inside a sealed bag for 30 minutes at 20° C. under standard test conditions. Only one repeat testing of each enzyme was performed to prove that all three types of enzyme can be successfully attached to the nylon beads.

After measuring the stains sheets on the spectrophotometer, the change in colour of the starch stain (stain 11) for amylase activity, the sebum and cocoa stains (stains 5 and 13 respectively) for lipase and the vegetable fat and milk stain (stain 12) for protease were of particular interest. The specific effects of the three enzymes are shown in Tables 9, 10 and 11.

TABLE 9

AMYLASE ACTIVITY ON NYLON 6,6 BEADS

| Sample - Amylase | Overall Amylase | Stain 11 |
|---|---|---|
| Unmodified beads, no chemistry | 4.70 | 4.64 |
| Unmodified beads, 1 mg/ml amylase (solution) | 6.65 | 11.40 |
| Treated beads, amylase, run 1 | 6.16 | 8.92 |

The amylase works particularly on starchy stains and as previously illustrated in Table 5, it is seen that stain 11 increases by 4 dE when washed with beads treated in amylase, which suggests that amylase has been successfully attached to the beads. The activity of the treated beads in the present example is seen to be lower than previously observed in Example 4, and shown in Table 5, due to the difference in having two layers of amylase compared to one layer of amylase.

TABLE 10

LIPASE ACTIVITY ON NYLON 6,6 BEADS

| Sample - Lipase | Stain 5 | Stain 13 |
|---|---|---|
| Unmodified beads, no chemistry | 3.90 | 10.58 |
| Unmodified beads, 1 mg/ml lipase (solution) | 5.87 | 12.22 |
| Treated beads, lipase, run 1 | 5.71 | 11.90 |

Stain 5 (sebum) and stain 13 (cocoa) appear to have better cleaning action when lipase treated beads are used when compared to unmodified beads. The lipase on the beads cleans equally as well as 1 mg/ml solution of lipase, thereby inferring that lipase is active while being combined with the nylon beads.

TABLE 11

PROTEASE ACTIVITY ON NYLON 6,6 BEADS

| Sample - Protease | Stain 9 | Stain 12 |
|---|---|---|
| Unmodified beads, no chemistry | 41.85 | 7.86 |
| Unmodified beads, 1 mg/ml protease (solution) | 45.12 | 14.54 |
| Treated beads, protease, run 1 | 44.32 | 8.29 |

The protease used in the examples is highly effective, as is apparent in the 1 mg/ml of solution, as it improved the cleaning of stain 12 (vegetable fat and milk) by 7 dE. While the treated beads do not have such a large effect on this stain, there is still a cleaning performance due to the presence of protease on the beads, as illustrated in FIG. 6.

Example 7

Enzymatic Cleaning

In the previous examples it was found that the activity of amylase decreased with each cycle. The hypothesis for this example is that the soil and sebum used in the simulated domestic wash test built up around the beads, thereby inhibiting the enzymatic action of amylase. For the present test, a small dose of standard detergent was added to the wash to decrease the build-up of soil on the amylase-treated beads, and to extend the lifetime of the amylase. A smaller decrease in amylase activity was observed when compared to tests carried out without detergent.

The nylon 6,6 beads were treated as described in Example 3 with borax, glutaraldehyde and amylase. The beads were then tested with 1 kg of ballast with 2 litres of water and 2 g of standard detergent in the horizontal axis sealed rotating drum apparatus adapted with a single agitator (lifter) at 20° C. for 30 minutes at an rpm of 50 in a sealed plastic bag. The standard detergent used was ECE non-phosphate reference detergent A (without optical brighteners) obtained from SDC Enterprises Ltd. One stain sheet and one sebum were also included in the test cycle and the stain sheets were measured as standard on the spectrophotometer.

It appears that the activity of amylase drops quite significantly after the first wash when washed without detergent. The results of washes with standard detergent and the effect of the detergent in apparently helping to reduce initial drop off of amylase activity are illustrated in FIG. 7.

On comparing the decrease in dE of treated beads cycled without detergent and the decrease in dE of treated beads cycled with detergent, a marked difference is noted and it is seen that the beads washed with detergent have much smaller changes in colour from one run to the next, as evidenced by the data in Table 12.

TABLE 12

COMPARISON OF WASHES WITH AMYLASE-TREATED BEADS IN FORMULATIONS WITH AND WITHOUT STANDARD DETERGENT

| Run | Treated beads (without detergent)/change in dE | Treated beads (with detergent)/change in dE |
|---|---|---|
| 1-2 | −2.92 | −1.18 |
| 2-3 | −1.06 | −1.76 |
| 3-4 | −3.39 | −0.42 |

Example 8

Enzymatic Cleaning

As in the previous example, this example sought to verify whether the enzyme immobilised on the beads was inhibited by a build-up of soil. The approach on this occasion was to use a batch of treated beads for four consecutive cycles, wash the beads with a non-ionic surfactant to remove the soil, and then assess the activity of immobilised amylase. The first test of washed beads showed an improvement of amylase activity compared to the last cycle before the wash.

The nylon 6,6, beads were treated following the using the ionic/polar bond layering methodology of Example 4. After cycling the beads under standard test conditions for 4 runs, the beads were washed with 4 ml of non-ionic surfactant in 2 L of water at 20° C. for 10 minutes at 15 rpm and rinsed in cold tap water, before being cycled for another 4 runs. The stain sheets were measured following the standard protocol on the Konica Minolta CM-3600A spectrophotometer with SpectraMagic NX software (UV component included, 8° aperture) and the dE values were generated.

The activity of stain 11 in terms of dE is shown in FIG. 8.

The centre four columns are the treated beads and the values gradually decrease with washing, as has been seen previously. The four columns to the right of the graph show the cleaning performance of the same beads after washing with non-ionic surfactant, from which it is seen that there is clearly a change in pattern, as the activity does not decrease as before but, rather, increases by nearly 1.5 dE after 4 more washes. It is noted that the ΔE value for all four runs after washing with non-ionic surfactant remain higher than the last run before washing with surfactant, the value for which is itself higher than for untreated beads.

Example 9

Enzymatic Cleaning

In the previous examples the beads were tested consecutively over a maximum of five days leaving a maximum of 48 hr between cycles. In this example it is shown that, if the beads are tested on a weekly basis, the activity of amylase is maintained for at least four weeks.

The example seeks to measure the rate of decline of amylase attached to nylon 6,6 beads when used on a weekly basis rather than an hourly basis. 2 kg of beads were treated in the horizontal axis sealed rotating drum apparatus adapted with a single agitator (lifter) following the procedure of Example 3, using a temperature of 80° C. for the first step and ambient temperature for steps 2 and 3. These beads were then utilised, once a week, in a washing procedure at 20° C. in a sealed plastic bag, as per the standard wash procedures previously described, then rinsed with cold tap water. The beads were stored between runs in a clear plastic sealed bag at room temperature, in a damp condition.

The results for the colour change of the overall amylase stains and the starch stain (stain 11) are shown in Table 13.

TABLE 13

CLEANING PERFORMANCE OF AMYLASE-TREATED BEADS AFTER STORAGE FOR 1-4 WEEKS

| Sample | Overall amylase/dE | Stain 11/dE |
|---|---|---|
| Unmodified beads - no chemistry | 3.54 | 3.15 |
| Week 1 | 5.24 | 8.57 |
| Week 2 | 5.20 | 7.18 |
| Week 3 | 5.13 | 8.05 |
| Week 4 | 4.75 | 7.45 |

It appears that the overall amylase activity remains fairly constant after the fourth week and so it may be assumed that the amylase is still attached to the beads in approximately the same activity as at each of the first to fourth weeks. It is apparent that attaching the amylase to the nylon beads provides a more stable environment for the amylase to persist, as opposed to a solution of amylase which is stored at room temperature for the same amount of time.

Example 10

Enzymatic Cleaning Using PET Beads

All the previous examples have involved tests using nylon 6,6 beads; this example was to show that amylase can be attached to other polymer beads, such as PET, using the general ionic/polar layering immobilisation technique of Example 4.

Thus, 2 kg of PET beads (supplied by Teknor, Apex, Oldbury, UK Grade PET 101) were incubated for two hours at room temperature in a solution of polymer 2. The beads were then rinsed in running cold tap water and then incubated for two hours at room temperature in a solution of polymer 1, after which the beads were rinsed in running cold tap water, and then incubated for two hours at room temperature in a solution of amylase. Finally the beads were rinsed in running cold tap water before testing in a simulated domestic wash as described above. The test results are shown in Table 14.

TABLE 14

CLEANING PERFORMANCE OF AMYLASE-TREATED PET BEADS

| Sample | Stain 11 (Starch)/dE |
|---|---|
| PET - water only | 5.91 |
| Treated PET with Amylase | 11.37 |

Example 11

Enzymatic Cleaning

This example involved immobilising amylase and lipase simultaneously on nylon 6,6 beads using the general ionic/polar layering immobilisation approach of Example 4, and was designed to show that amylase and lipase can be attached simultaneously on nylon 6,6 beads and have an effect on a simulated domestic wash.

Thus, using the method of Example 4, nylon 6,6 beads were treated firstly with polymer 1 and then a mixture containing equal amounts of lipase and amylase (1 mg/ml of each solution) was added to the beads in the same manner before the beads were rinsed with cold tap water.

The results on stain 5 (sebum) and stain 11 (starch) are shown in FIGS. 9 and 10.

Example 12

Enzymatic Cleaning Using PET Beads

This example was designed to explore the direct interaction of amylase with the surface of PET without the inclusion of polymer layers and to show the effect of the resulting beads on a simulated domestic wash.

2 kg of PET beads were incubated for two hours at room temperature in a 1 mg/ml solution of amylase in phosphate buffer solution (pH 7.4). The beads were then rinsed thoroughly in running cold tap water and tested in a simulated domestic wash as described previously. The results are presented in Table 15.

TABLE 15

CLEANING PERFORMANCE OF AMYLASE-TREATED PET BEADS

| Sample | Stain 11 (Starch)/dE |
|---|---|
| PET - water only | 5.91 |
| Treated PET with Amylase | 10.89 |

Comparative Example 13

Enzymatic Immobilisation on PP Beads

In this example, polypropylene beads were treated using various methods of the ionic/polar layering immobilisation technique of Example 4 in order to establish that this method requires the use of a polar polymer in order to facilitate effective interaction and allow for interaction.

Thus, 10 g of polypropylene beads (PP—SABIC 575P, general purpose injection moulding homopolymer grade) were treated with amylase using the ionic/polar layering immobilisation technique using the configurations below:

A. PP+Polymer 1+Amylase sol
B. PP+Polymer 2+Polymer 1+Amylase sol
C. PP+Amylase
D. PP+Phosphate buffer solution as a negative control with beads In the above formulations polymer 1 and polymer 2 were as previously described. 10 ml of a 1 mg/ml amylase solution was used as a positive control and 10 ml of deionised water was used as a negative control. The beads were then tested using a modified Phadebas® test and provided the results which are shown in FIG. 11.

Example 14

Bleaching

Nylon 6,6 beads were treated using the approach of Example 3 to show that the bleaching effect of sodium perborate is retained over three washes and washing was performed in an industrial washer/extractor.

Fabric cleaning cycles were carried out using an apparatus as described in WO-A-2011/098815. This apparatus was based on a 50 kg Sea Lion industrial washer-extractor, modified to run with polymeric particles. The second chamber, pumping means, separating means, and rotatably mounted cylindrical cage in the apparatus, were all as specified in the 'Generation 2 Prototype' design, developed by Xeros Ltd., Sheffield, UK in 2011. The polymeric particles were Technyl (Nylon) grade XA193, as supplied by Solvay, Lyon, France. The mass of particles in the apparatus was 35 kg. Sodium perborate tetrahydrate (3 kg; supplied by Univar, Middlesbrough, UK) was used, where specified, by manual addition to the washer extractor drum. Fabric washing cycles used 20.0 kg of clean, dry, standard BS ballast (according to BS EN 60456: 2011), as supplied by EMPA, St. Gallen, Switzerland. Stains were added to the wash load to assess cleaning performance—5 off WFK PCMS-55_05-05x05 Standard Industry/Commercial Laundry Stain Monitors, plus 5 off WFK SBL2004 simulated sebum grease stain sheets. The wash cycles were run at wash temperatures of 40° C., followed by three rinses. The results are shown in Table 16 and FIG. 10.

TABLE 16

BLEACHING PERFORMANCE OF SODIUM PERBORATE TREATED BEADS COMPARED TO UNTREATED BEADS

| | Description | All Bleachable stains dE | Stain 3. Red wine aged dE | Stain 6. Curry dE | Stain 9. Blood aged dE |
|---|---|---|---|---|---|
| Sample 1 | Beads - no chemistry | 19.72 | 21.21 | 3.99 | 45.55 |
| Sample 2 | Beads + sodium perborate | 28.14 | 31.24 | 16.04 | 56.18 |
| Sample 3 | Beads from sample 2 re-washed | 25.62 | 25.64 | 11.52 | 54.61 |

TABLE 16-continued

BLEACHING PERFORMANCE OF SODIUM PERBORATE TREATED BEADS COMPARED TO UNTREATED BEADS

| | Description | All Bleachable stains dE | Stain 3. Red wine aged dE | Stain 6. Curry dE | Stain 9. Blood aged dE |
|---|---|---|---|---|---|
| Sample 4 | Beads from sample 3 re-washed | 21.94 | 22.06 | 7.52 | 49.22 |

The results therefore demonstrate that treatment with bleaching agents such as sodium perborate can be retained for at least three washes in a commercial washer extractor.

Hence, it has been found that it is possible to treat Nylon 6,6 beads with enzymes and/or bleaching agents to chemically bond these chemical agents to the beads, either by means of covalent bonds or by means of ionic or polar bonds, or other chemical bonds formed by virtue of unequal charge distributions between polymeric particles and immobilised materials; typically, these polarised bonds are formed by means of layered structures.

Beads treated with amylase have shown a positive effect on a starch/pigment stain compared to untreated beads tested under the same conditions. Furthermore, amylase treated beads maintained a positive effect on the washing performance of a starch stain over four weeks.

Bleaching agents immobilised on nylon beads have also shown a positive effect on the wash performance of bleach sensitive stains.

It has also been observed that used treated-beads appeared to recover part of their amylase activity when washed with a solution of non-ionic surfactant.

In addition, it was seen to be possible to attach lipase and protease on nylon 6,6 beads using an ionic/polarised bond layered approach. This approach also allowed amylase to be immobilised on PET, and made it possible to immobilise amylase and lipase simultaneously, and to show a positive effect on both a lipase monitor stain and an amylase monitor stain.

However, a modified Phadebas® test on polypropylene beads showed no active amylase when the beads were treated by the ionic/polarised bond layered approach with a solution of amylase and polymer 1, followed by a solution of amylase. When treated with a solution of polymer 2, followed by a solution of polymer 1, followed by a solution of amylase, the modified Phadebas® test showed minimal activity present on the beads (approximately $\frac{1}{30}^{th}$ of the amylase solution control).

Finally, it has been demonstrated that treatment with bleaching agents such as sodium perborate can be retained for at least three washes in a commercial washer extractor.

Additionally, it seems to be the case that the retained bleaching effect over a number of washes does not require pre-activation (i.e. pre-treatment of the beads in the washing machine sump with an oxidising agent). This suggests that any treatment of nylon beads with an oxidising agent (e.g. perborate, percarbonate, peroxide etc.), which are regularly found in standard laundry detergents) automatically gives additional cleaning performance benefits over subsequent washes. In other words, there appears to be a synergistic interaction between nylon beads and oxidising agents in terms of cleaning performance.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method for the cleaning of a soiled substrate, said method comprising laundry treatment of the soiled substrate with a cleaning formulation comprising a multiplicity of solid cleaning particles, wherein said solid cleaning particles comprise polymeric particles and at least one cleaning agent, wherein said at least one cleaning agent comprises at least one enzyme, oxidising agent or bleach, wherein said at least one cleaning agent is immobilised on a surface of said polymeric particles, wherein the polymeric particles comprise polar groups and wherein the polymeric particles are initially treated with at least one activating agent in order to modify the chemical properties at the surfaces of the polymeric particles, with subsequent treatment or reaction of the at least one cleaning agent with the modified particles, wherein said treatment with at least one activating agent comprises treatment with at least one polar group-containing material, such that the at least one polar group-containing material and at least one cleaning agent are applied to said polymeric particles in layers, and said at least one cleaning agent is bonded to the polymeric particles by immobilisation thereon by means of ionic and/or polar bonds and/or other chemical bonds formed by virtue of unequal charge distributions between the polymeric particles and layers of immobilised polar group-containing material and cleaning agent.

2. A method as claimed in claim 1 wherein said method is performed in an aqueous environment in the presence of water, wherein water is added to the system so as to provide a water to substrate ratio which is between 2.5:1 and 0.1:1 w/w.

3. A method as claimed in claim 1 wherein said solid cleaning particles are added at a particle to substrate addition level of 0.1:1-30:1 by dry mass of substrate.

4. A method as claimed in claim 1 wherein said soiled substrate comprises a textile fibre or leather, optionally wherein said textile fibre comprises a natural fibre or a synthetic textile fibre or a blend thereof.

5. A method as claimed in claim 1 wherein said soiled substrate comprises a textile fibre and wherein said laundry treatment is performed at temperatures of between 5 and 95° C. for a duration of between 10 minutes and 1 hour.

6. A method as claimed in claim 1 wherein said solid cleaning particles are re-used in further procedures according to the claimed method.

7. A method as claimed in claim 1 wherein said solid polymeric cleaning particles comprise polyalkenes, polyamides, polyesters or polyurethanes, and/or wherein said solid polymeric cleaning particles comprise copolymers comprising monomers which are ionically charged or include polar moieties or unsaturated organic groups.

8. A method as claimed in claim 1 wherein said at least one cleaning agent comprises at least one detergent and/or wherein said at least one cleaning agent additionally comprises builders, chelating agents, dye transfer inhibiting agents, dispersants, enzyme stabilizers, catalytic materials, bleach activators, polymeric dispersing agents, clay soil removal agents and/or suds suppressors, optionally wherein said at least one detergent comprises at least one surfactant which is selected from non-ionic and/or anionic and/or cationic surfactants and/or ampholytic and/or zwitterionic and/or semi-polar non-ionic surfactants.

9. A method as claimed in claim 1, said at least one activating agent comprises at least one polar group-containing material and said at least one cleaning agent comprises at least one enzyme, optionally wherein said polymeric particles comprise particles of Nylon 6,6 or poly(ethylene terephthalate), and/or optionally wherein said at least one polar group-containing material comprises gelatin, starch, cellulose, chitosan, chitan, carboxymethylcellulose, poly(vinylimidazoles), poly(acrylic acid), poly(methacrylic acid), poly(lactic acid), poly(maleic acid), poly(glycolic acid), poly(acrylonitrile), poly(vinylpyrrolidone), poly(dimethylaminoethyl methacrylate), poly(ethylene imine), poly(allylamine), poly(allylamine) hydrochloride, poly(ethylene glycol), poly(propylene glycol), poly(acrylamide), poly(vinyl alcohol), poly(vinyl acetate), poly(vinyl formamide), poly(vinylamine), amine-containing molecules, carboxylic acids, and carboxylic acid-containing polymers, as well as derivatives and copolymers thereof.

10. A method as claimed in claim 9 wherein said at least one enzyme comprises lipase, protease and/or amylase.

11. A method as claimed in claim 1 wherein said polymeric solid cleaning particles have an average density in the range of 0.5-2.5 g/cm$^3$ and an average volume in the range of 5-275 mm$^3$.

12. A method as claimed claim 1 wherein said at least one cleaning agent is bonded to the polymeric particles by immobilisation thereon by means of ionic bonds.

13. A method as claimed in claim 1, wherein said method is performed in an aqueous environment in the presence of water and wherein said solid cleaning particles are re-used in further procedures according to the claimed method.

14. A cleaning formulation comprising a multiplicity of solid cleaning particles, wherein said solid cleaning particles comprise polymeric particles and at least one cleaning agent, wherein said cleaning agent comprises at least one enzyme, oxidising agent or bleach, wherein said at least one cleaning agent is immobilised on the surface of said polymeric particles, wherein the polymeric particles comprise polar groups and wherein the polymeric particles are initially treated with at least one activating agent in order to modify the chemical properties at the surfaces of the polymeric particles, with subsequent treatment or reaction of the at least one cleaning agent with the modified particles, wherein said treatment with at least one activating agent comprises treatment with at least one polar group-containing material, such that the at least one polar group-containing material and the at least one cleaning agent are applied to said polymeric particles in layers, and said at least one cleaning agent is bonded to the polymeric particles by immobilisation thereon by means of ionic and/or polar bonds and/or other chemical bonds formed by virtue of unequal charge distributions between the polymeric particles and layers of immobilised polar group-containing material and cleaning agent.

* * * * *